US011235104B2

(12) United States Patent
Cowe et al.

(10) Patent No.: US 11,235,104 B2
(45) Date of Patent: Feb. 1, 2022

(54) MEDICAMENT DELIVERY DEVICES

(71) Applicant: Owen Mumford Limited, Oxford (GB)

(72) Inventors: Toby Cowe, Oxfordshire (GB); Timothy Evans, Oxfordshire (GB)

(73) Assignee: Owen Mumford Limited, Oxford (GB)

( * ) Notice: Subject to any disclaimer, the term of this patent is extended or adjusted under 35 U.S.C. 154(b) by 139 days.

(21) Appl. No.: 16/483,661

(22) PCT Filed: Feb. 6, 2018

(86) PCT No.: PCT/GB2018/050334
§ 371 (c)(1),
(2) Date: Aug. 5, 2019

(87) PCT Pub. No.: WO2018/142167
PCT Pub. Date: Aug. 9, 2018

(65) Prior Publication Data
US 2019/0366000 A1 Dec. 5, 2019

(30) Foreign Application Priority Data
Feb. 6, 2017 (GB) ..................... 1701935

(51) Int. Cl.
*A61M 5/20* (2006.01)
*A61M 5/24* (2006.01)
*A61M 5/32* (2006.01)
(52) U.S. Cl.
CPC ........ *A61M 5/2033* (2013.01); *A61M 5/2422* (2013.01); *A61M 5/3234* (2013.01); *A61M 2005/2073* (2013.01)
(58) Field of Classification Search
CPC .............. A61M 5/2033; A61M 5/2422; A61M 5/3234; A61M 2005/2073; A61M 5/322;
(Continued)

(56) References Cited

U.S. PATENT DOCUMENTS

2013/0317432 A1 11/2013 Fabien et al.
2014/0330216 A1* 11/2014 Weaver ............... A61M 5/3232
604/198
2016/0001004 A1* 1/2016 Fourt ................... A61M 5/2033
604/198

FOREIGN PATENT DOCUMENTS

EP 2 438 942 4/2012
EP 2 468 332 6/2012
(Continued)

OTHER PUBLICATIONS

May 16, 2018 Transmittal of ISR and Written Opinion of Int'l Searching Authority for PCT/GB2018/050334.

*Primary Examiner* — Bhisma Mehta
*Assistant Examiner* — Neeraja Gollamudi
(74) *Attorney, Agent, or Firm* — Quarles & Brady LLP

(57) ABSTRACT

A medicament delivery device (100; 300; 400) comprises a chassis (124), a drive element (166) for driving a stopper (22) to expel the medicament through a cannula (144). A carrier (126) is arranged for movement with respect to the chassis (124). Insertion means (130, 202) biases the carrier (126) in an insertion direction. A control part (132) is biased for rotation with respect to the carrier (126). A locking element (176) prevents rotation of the control part (132) in an initial state. The locking element (176) is coupled to the drive element (166) such that the control part (132) is released for rotation when the drive element (166) reaches an activation position during a delivery stroke. Rotation of the control part (132) through a predetermined angle causes decoupling of the insertion means (130, 202) from the carrier (126) to allow movement of the carrier (126) in a retraction direction after the end of the delivery stroke.

27 Claims, 25 Drawing Sheets

(58) Field of Classification Search
CPC .......... A61M 5/31578; A61M 5/31583; A61M 2005/208; A61M 2005/206
See application file for complete search history.

(56) References Cited

FOREIGN PATENT DOCUMENTS

| | | | |
|---|---|---|---|
| EP | 2 468 337 | 6/2012 | |
| EP | 2468337 A1 * | 6/2012 | .............. A61M 5/20 |
| EP | 2 583 705 | 4/2013 | |
| WO | 2003097133 A1 | 11/2003 | |
| WO | WO 2014/159017 | 10/2014 | |
| WO | 2017009640 A1 | 1/2017 | |

* cited by examiner

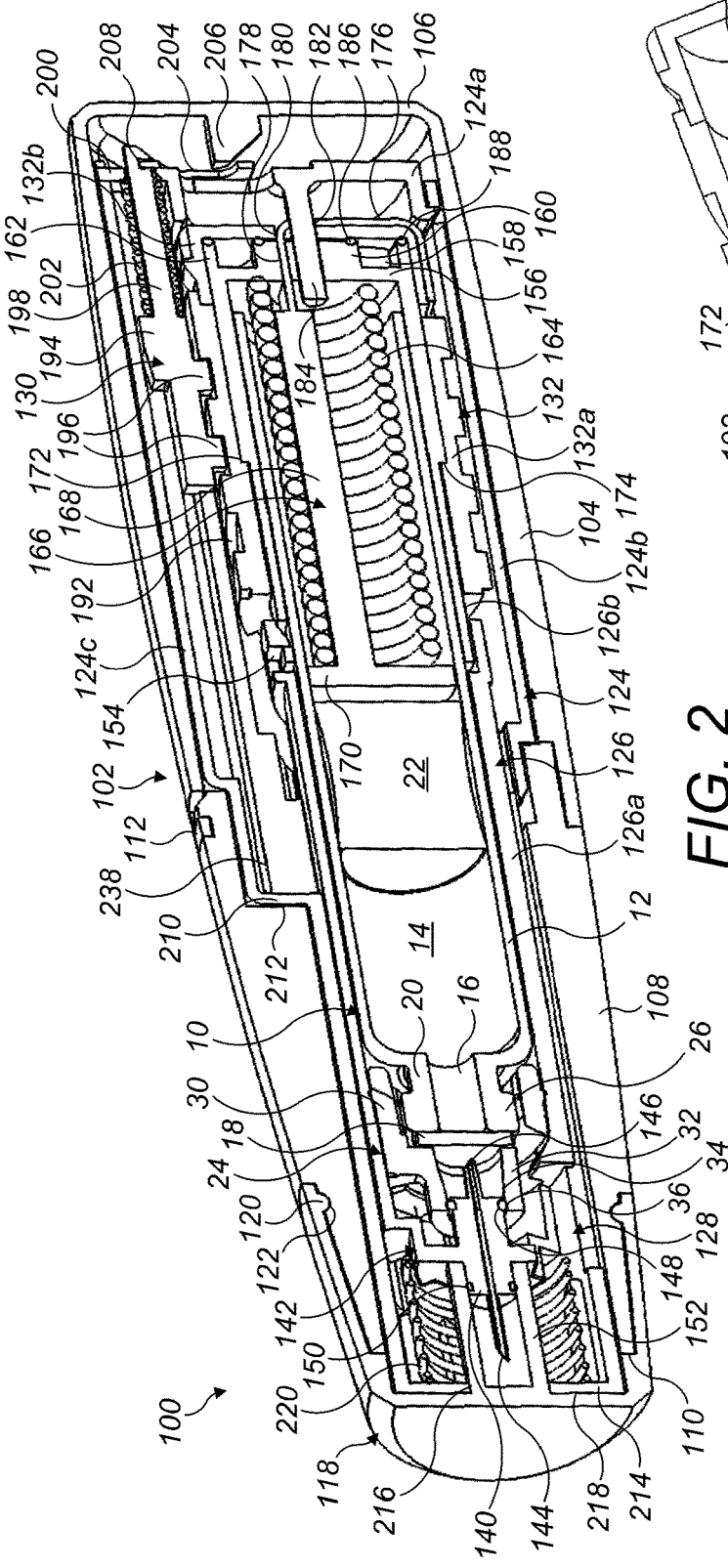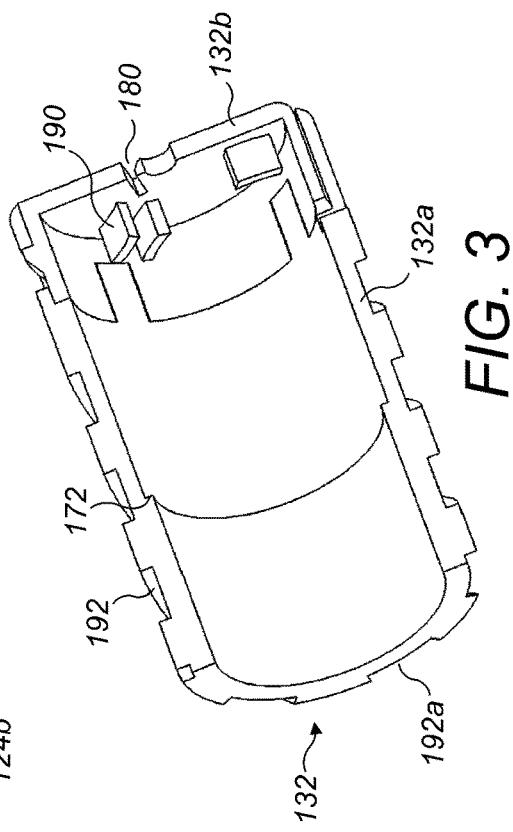

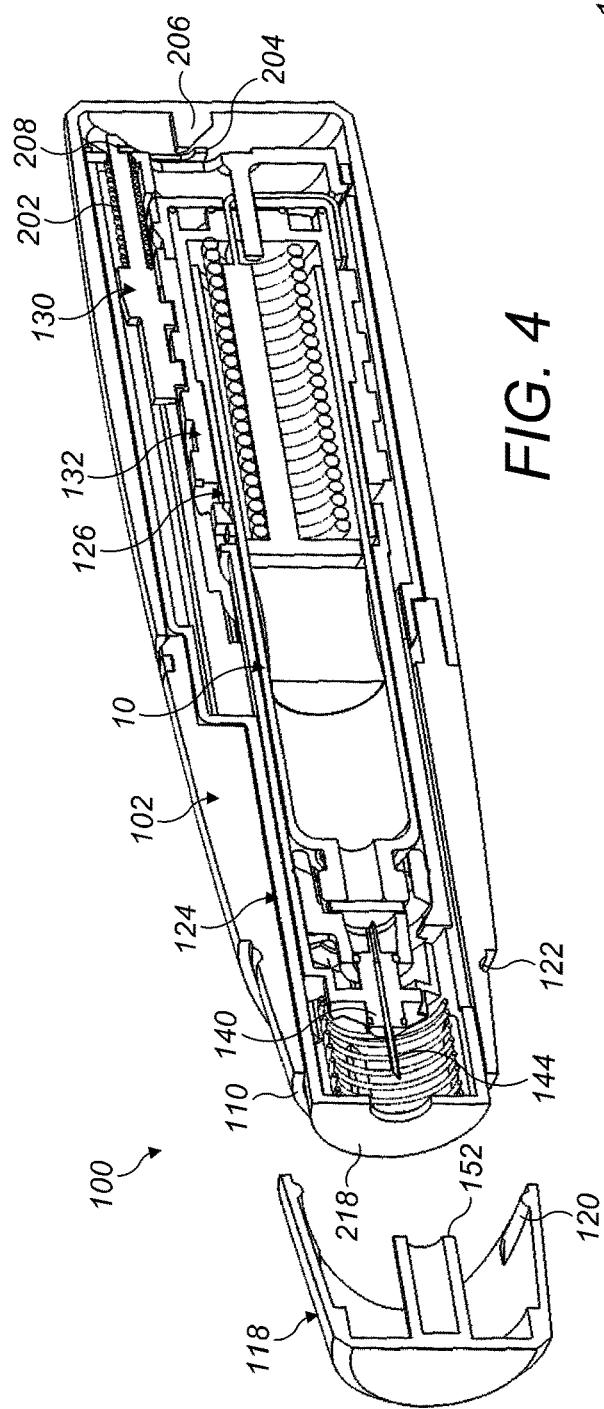
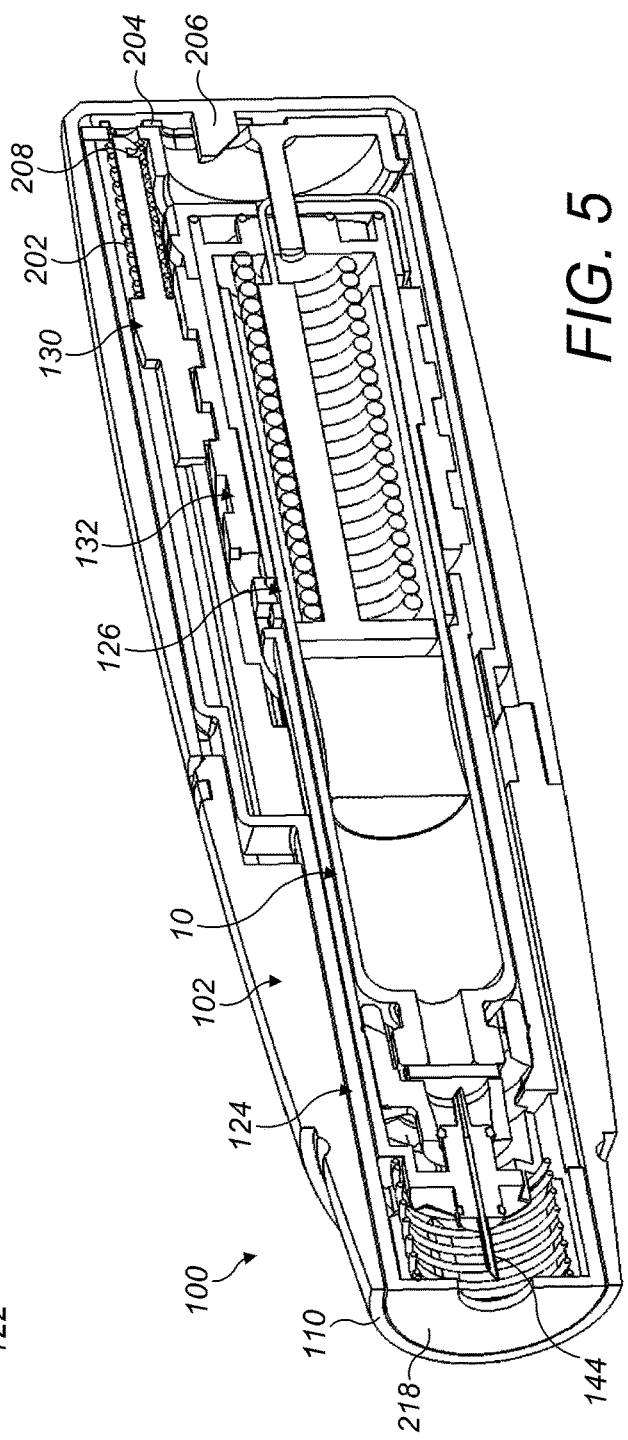

MEDICAMENT DELIVERY DEVICES

The present application is a § 371 submission of international application no. PCT/GB2018/050334, filed 6 Feb. 2018 and titled Medicament Delivery Devices, which was published in the English language on 9 Aug. 2018 with publication no. WO 2018/142167 A1, and which claims the benefit of the filing date of GB 17 01935.7 filed 6 Feb. 2017, the contents of which are incorporated herein by reference.

This invention relates to devices suitable for delivering medicament substances to a patient. In particular, but not exclusively, the invention relates to medicament delivery devices for the subcutaneous delivery of medicaments with a relatively high viscosity. This invention further relates to medicaments, including pharmaceutical compositions, for subcutaneous injection or infusion disposed within the delivery devices and methods of treating patients with conditions susceptible to treatment by delivering the medicament using the delivery devices described herein.

Medicaments for subcutaneous injection or infusion are used in therapy in various different clinical situations. Administration of medicaments by a patient themselves (self-administration) or by a carer who is not medically trained is becoming increasingly important for reducing care costs and reducing patient dependency on clinical staff and facilities.

To this end, a variety of devices have been developed that are suitable for delivery of injectable medicaments in a non-clinical environment by a patient or carer. Typically, in such devices, at least part of the operational sequence of the device is automated.

For example, injection devices designed for automatic needle insertion and injection of a single pre-determined dose of a medicament are known in the art as auto-injectors. Such devices typically include a housing that allows the user to grip the device, a pre-filled syringe containing the medicament, and a drive mechanism. The pre-filled syringe includes a tubular glass barrel with a staked hypodermic needle at its distal end, a rigid needle shield to protect and seal the needle, and a stopper slidably received in the barrel. One example of a pre-filled syringe of this type is available under the registered trade mark Hypak (Becton Dickinson, New Jersey, USA).

The syringe is axially movable within the housing between an initial, retracted position in which the needle is retracted in the housing, and a deployed position in which the needle projects from the distal end of the housing. With the syringe in the retracted position, the distal end of the housing is closed by a cap. To prepare the device for use, the cap is removed. The cap is arranged to grip the needle shield, so that removal of the cap pulls the needle shield off the needle. The distal end of the housing is then placed against the skin, and the user operates a trigger of the device, such as a button, to activate the drive mechanism. The drive mechanism typically comprises a plunger that is biased in the distal direction by a compression spring. The plunger is initially held in an initial, latched position by a latch arrangement. Upon activation of the drive mechanism, the plunger is released from the latched position and can move distally under the force of the compression spring.

Movement of the plunger first causes the syringe to move from the retracted position into the deployed position, so that the needle pierces the skin. Subsequently, the plunger forces the stopper in the distal direction to inject the medicament.

In some known devices, after injection of the medicament, the needle is automatically withdrawn from the injection site and retracted into the body of the device, to shroud the needle after use. Typically, retraction of the needle is driven by a spring that acts to move the syringe in the proximal direction after the medicament dose has been delivered.

In devices that incorporate automatic needle retraction, it is important that the needle is not retracted before the whole dose of medicament has been delivered, since premature retraction of the needle could result in an under dose of the medicament and a "wet" injection, where medicament is spilled from the device after removal from the injection site.

The present applicant's International Patent Application Publication No. WO 03/097133 A1 discloses an auto-injector device in which operation of an operating button triggers sequential needle insertion, medicament delivery and needle retraction steps. In this case, the plunger of the device incorporates a lost motion arrangement so that the drive spring continues to apply a distal force to the syringe for a short period after the stopper of the syringe has reached the distal end of its travel. The drive spring then decouples from the syringe to allow a retraction spring to move the syringe in the proximal direction. In this way, needle retraction does not occur until after the full dose of the medicament has been delivered. The device of WO 03/097133 A1 thus provides a simple arrangement in which needle insertion, medicament delivery and needle retraction are performed automatically and with low risk of premature needle retraction.

It has recently become desirable to provide injection devices that are suitable for the delivery of relatively viscous medicaments. The use of viscous medicaments can increase the likelihood of premature needle retraction, since the medicament takes longer both to flow through the needle and to diffuse within the injection site.

Furthermore, as it is generally undesirable to increase either the size of the needle or the duration of the injection, a higher-force drive spring is usually required to drive medicament delivery. In the device described in WO 03/097133 A1, the use of a higher-force spring in combination with a high viscosity medicament could reduce the effect of, or even defeat, the arrangement for preventing premature needle retraction.

Furthermore, in arrangements in which a single drive spring drives both needle insertion and medicament delivery, the force applied to the syringe for needle insertion increases with the force of the drive spring. Accordingly, such arrangements are less preferred for the delivery of viscous medicaments, since the requirement for a higher-force drive spring could result in increased patient discomfort during needle insertion, undesirable noise during operation, and the potential for damage to the device.

It would therefore be desirable to provide a medicament delivery device having automatic needle insertion, medicament delivery and needle retraction operations that is suitable for use with relatively high viscosity medicaments.

Furthermore, the device described in WO 03/097133 A1 and the majority of other known devices that incorporate an automatic needle retraction mechanism apply the retraction force to the needle by way of the syringe body. Although use of a prefilled syringe is often convenient, in some cases it may be desirable to package the medicament within the device in a different type of container, such as a cartridge. It would therefore also be desirable to provide a medicament delivery device having an automatic needle retraction mechanism that can be used with cartridge-type medicament containers.

Against this background, and from one aspect, the present invention resides in a medicament delivery device for delivery of medicament from a container into an injection site through a cannula, the device comprising a chassis, a drive element for driving a stopper of the container in a delivery stroke to expel the medicament through the cannula, a carrier arranged for movement with respect to the chassis in an insertion direction to advance the cannula from the device and in a retraction direction to withdraw the cannula after delivery of the medicament, and insertion means coupled to the carrier for biasing the carrier in the insertion direction. The device further comprises a control part biased for rotation with respect to the carrier, and a locking element cooperable with the control part for preventing rotation of the control part with respect to the carrier in an initial state of the device. The locking element is coupled to the drive element such that the control part is released for rotation when the drive element reaches an activation position during the delivery stroke, and rotation of the control part through a predetermined angle with respect to the carrier causes decoupling of the insertion means from the carrier to allow movement of the carrier in the retraction direction after the end of the delivery stroke.

With this arrangement, withdrawal of the cannula from the injection site does not take place as soon as the drive element reaches the activation position. Instead, retraction of the cannula is delayed by the time taken for the control part to rotate through the predetermined angle, ensuring that the full dose of medicament can be delivered through the cannula and allowing time for the medicament to dissipate within the injection site. Furthermore, because the insertion means acts on the carrier, rather than the drive element, to advance the cannula, the force applied by the insertion means can be relatively low to reduce patient discomfort during cannula insertion and the risk of damage to the device. A relatively high force can be applied to the drive element, for example to deliver a medicament with relatively high viscosity.

To increase the time delay before retraction of the cannula, the device may comprise retarding means for controlling the speed of rotation of the control part. For example, the retarding means may comprise a rotational damper. In some embodiments, the device comprises a chamber for receiving a viscous substance and at least one vane arranged for movement through the viscous substance upon rotation of the control part with respect to the carrier. The chamber may be defined at least in part by the carrier and at least in part by the control part. In this way, a simple and compact arrangement can be achieved. In other embodiments, the device comprises a chamber for receiving a viscous substance and at least one projection arranged to constrict movement of the viscous substance through the chamber upon rotation of the control part with respect to the carrier.

The locking element may be engageable with the control part to prevent rotation of the control part with respect to the carrier. In this case, the locking element may disengage from the control part when the drive element reaches the activation position, to allow rotation of the control part. For example, in one arrangement, the locking element is engageable with an opening, such as a slot, in the control part, and the locking element withdraws from the opening when the drive element reaches the activation position.

The locking element may be deformable or flexible to adopt a non-linear storage configuration in an initial state of the device, to provide a compact arrangement. For example, the locking element may be threaded through an opening in the control part and then folded around the control part and/or other device components. The flexible locking element can then be pulled back through the opening to withdraw the locking element from the opening and allow rotation of the control part. Such an arrangement requires a substantially shorter length than would be the case if the locking element were rigid. To this end, the locking element may comprise a flexible strip. In any case, the locking element may comprise an elongate extension of the drive element.

In some embodiments, the locking element may be provided as an elongate member slidably coupled to the drive element. For example, the locking element may comprise a channel or track for receiving the shaft of the drive element in a telescopic coupling. In embodiments, the length of the slidable extremity of the telescopic coupling may, at least in part, define the activation position where the locking element releases the control part.

The drive element preferably reaches the activation position before the end of the delivery stroke. This ensures that the locking element always releases the control part, accounting for possible manufacturing variations and tolerances.

The device may comprise retaining means for holding the drive member in a starting position with respect to the carrier and for releasing the drive member to start the delivery stroke. The retaining means is preferably arranged to release the drive member after movement of the carrier in the insertion direction. In this way, the delivery stroke is automatically initiated once the cannula has been inserted, without further user action being required.

In one arrangement, the retaining means comprises a retaining member for engagement with the locking element to hold the drive member in the starting position, and movement of the carrier in the insertion direction with respect to the chassis causes disengagement of the retaining member from the locking element. For example, the locking element may comprise an aperture for receiving the retaining member. Preferably, the chassis comprises the retaining member.

In one arrangement, the retaining means may further comprise a latching arm connected to the drive member. The latching arm may engage between the carrier and the retaining member in the starting position for preventing distal movement of the drive member. For example, in one arrangement, the latching arm may be engaged with the carrier and/or the control part, and the engagement of the retaining member with the locking element in the starting position may prevent the latching arm from disengaging of from this latched position.

The control part may be rotatable around a longitudinal axis of the carrier, and/or the control part may be disposed concentrically around the carrier. For example, the control part may comprise a sleeve disposed around the carrier. In these ways, a particularly compact device can be provided.

The control part may be coupled to the carrier for joint axial movement at least in the insertion direction. The control part may be coupled to the carrier for joint axial movement in both the insertion and retraction directions.

The insertion means may be coupled to the carrier by way of the control part, and the coupling member may disengage from the control part upon rotation of the control part through the predetermined angle. For example, the insertion means may comprise a coupling member for engagement with the control part, and an insertion spring for biasing the coupling member in the insertion direction.

The control part may comprise an inclined formation for engagement with the coupling member, such that the coupling member biases the control part for rotation with respect to the carrier. In this way, rotation of the control part can be driven by the insertion means, avoiding the need to provide an additional spring or other component for driving rotation of the control part. In one arrangement, the inclined formation comprises a helical track.

The device may include latch means for holding the carrier in an initial position with respect to the chassis, and a trigger that is operable to release the latch means to allow movement of the carrier in the insertion direction.

For example, when the insertion means comprises a coupling member, the latch means may comprise a latch member operable to latch the coupling member to the chassis to hold the carrier in the initial position and to release the coupling member from the chassis upon operation of the trigger. The latch member may be moveable laterally with respect to the insertion direction to release the coupling member. For example, the latch member may be mounted on an end wall of the chassis.

In another example, the latch means comprises a latch member operable to latch the carrier to the chassis and to release the carrier from the chassis upon operation of the trigger. In this case, the latch member may comprise a latching arm for engagement with a surface of the chassis.

A trigger component, such as a button or slider, may be provided to operate the trigger, in which case the chassis may act as a casing for the device. Preferably, however, the device includes a casing for receiving the chassis. The casing may be moveable in the insertion direction with respect to the chassis to operate the trigger to release the latch means. For example, the trigger may be disposed on an inner surface of the casing. In these ways, the length of the device can be minimised.

In some embodiments, a chassis locking mechanism may be provided between the casing and the chassis for lockably connecting the casing to the chassis once the casing has moved in the insertion direction. In this way, once the device has been triggered, the casing and chassis axially lock together to prevent any forces that may be applied by the internal spring mechanisms from acting to drive the casing proximally away from the injection site.

To guard against unintentional operation of the device, the device may comprise a removable cap for closing an end of the casing and for preventing movement of the casing with respect to the chassis while the cap is attached to the casing. The cap may comprise sealing means for maintaining the sterility of the cannula prior to removal of the cap. The end of the casing may include an aperture for receiving the sealing means of the cap. In one embodiment, the device further comprises a latching mechanism between the casing and the chassis for preventing movement of the casing with respect to the chassis, wherein the removable cap prevents disengagement of the latching mechanism while the cap is attached to the casing. For example, the removable cap may comprise at least one finger for preventing deflection of the latch from its engaged position.

Although the device is suitable for use with a pre-filled syringe that includes a staked cannula in the form of a needle, in a preferred embodiment the carrier of the device comprises a cannula holder for retaining the cannula, which is preferably a hypodermic needle. In this case, the container may comprise a cartridge having a sealing element for closing an outlet of the cartridge, and the device may comprise a sealing element release member that is cooperable with the sealing element to open the outlet and to establish a flow path from the cartridge to the cannula. With such an arrangement, the device can be used with cartridges that can also be used in different types of delivery device. Furthermore, this arrangement avoids the need for a relatively large rigid needle shield for sealing the distal end of the cannula, as is typically used in pre-filled syringes. Instead, a substantially shorter means for sealing the cannula can be provided, for example as part of a removable cap as previously described. In this way, the length of the device can be minimised. The diameter of the sealing means in this arrangement can also be smaller than the diameter of a rigid needle shield, for example to minimise the size of the aperture in the casing that is required to receive the sealing means.

The carrier may be arranged to retain the cartridge in a first position in which the outlet is closed, and the cartridge may be movable with respect to the carrier into a second position to open the outlet to allow delivery of the medicament. A seal arrangement may be provided for maintaining sterility of the sealing element release member when the cartridge is in the first position.

The device may include a drive spring for biasing the drive element for movement with respect to the carrier. Preferably, to provide a compact arrangement, the drive spring acts between an end wall of the carrier and the drive element. Similarly, the device may include a retraction spring for moving the carrier in the retraction direction upon decoupling of the insertion means.

According to another aspect of the present invention, there is provided a medicament delivery device for delivery of medicament from a container into an injection site through a cannula, the device comprising: a chassis; a drive element biased for driving a stopper of the container in a delivery stroke to expel the medicament through the cannula; a carrier arranged for movement with respect to the chassis in an insertion direction to advance the cannula from the device; a coupling member coupled to the carrier; an insertion spring for biasing the coupling member in the insertion direction; a latch member operable to latch the coupling member to the chassis to hold the carrier in the initial position and to release the coupling member from the chassis upon operation of a trigger for driving the carrier in the insertion direction; a sealing element release member engageable with the container for piercing a sealing element part of the container to establish a flow path from the container to the cannula; and retaining means for holding the drive element in a starting position with respect to the carrier and for releasing the drive element to initiate the delivery stroke once the carrier has moved a predetermined distance with respect to the chassis under the influence of the insertion spring; wherein, on release of the drive element, the driving of the stopper moves the container relative to the carrier to engage sealing element release member with the container for piercing the sealing element. In this way, the movement of the carrier under the force applied by the insertion spring acts to release the drive element, which in turn pierces the container. Furthermore, the retaining means allows control over the point during the insertion stroke at which the container is pierced. For example, the predetermined distance at which the retaining means releases the drive element may be set to substantially correspond to the distance in an insertion direction for the carrier to move for advancing the cannula into the injection site. In this way, the piercing of the container may be delayed until the cannula has been fully inserted into the patient.

Medicaments, including pharmaceutical compositions, contemplated for use in the delivery device may comprise small molecules, vaccines, live or attenuated cells, oligonucleotides, DNA, peptides, antibodies, and recombinant or naturally occurring proteins, whether human or animal, useful for prophylactic, therapeutic or diagnostic application. The active ingredient can be natural, synthetic, semisynthetic or derivatives thereof. A wide range of active ingredients are contemplated. These include, for example, hormones, cytokines, hematopoietic factors, growth factors, antiobesity factors, trophic factors, anti-inflammatory factors, and enzymes. The pharmaceutical compositions also may include, but are not limited to, insulin, gastrin, prolactin, human growth hormone (hGH), adrenocorticotropic hormone (ACTH), thyroid stimulating hormone (TSH), luteinizing hormone (LH), follicle stimulating hormone (FSH), human parathyroid hormone (PTH), glucagon, glucagons-like peptide 1 (GLP-1), glucagons-like peptide 2 (GLP-2), insulin-like growth factors (IGFs) such as insulin growth factor I (IGF I), insulin growth factor II (IGF II), growth hormone-releasing factor (GRF), human chorionic gonadotropin (HCG), gonadotropin-releasing hormone, motilin, interferons (alpha, beta, gamma), interleukins (e.g., IL-1, IL-2, IL-4, IL-5, IL-6, IL-9, IL-11, IL-12, IL-13, IL-15, IL-16, IL-17, IL-18, IL-20 or IL-21), interleukin-1 receptor antagonists (IL-Ira), tumor necrosis factor (TNF), tumor necrosis factor-binding protein (TNF-bp), CD40L, CD30L, erythropoietin (EPO), plasminogen activator inhibitor 1, plasminogen activator inhibitor 2, von Willebrandt factor, thrombopoietin, angiopoietin, granulocyte-colony stimulating factor (G-CSF), stem cell factor (SCF), leptin (OB protein), brain derived neurotrophic factor (BDNF), glial derived neurotrophic factor (GDNF), neurotrophic factor 3 (NT3), fibroblast growth factors (FGF), neurotrophic growth factor (NGF), bone growth factors such as osteoprotegerin (OPG), transforming growth factors, epidermal growth factor (EGF), vascular endothelial growth factor (VEGF), macrophage colony stimulating factor (M-CSF), granulocyte macrophage colony stimulating factor (GM-CSF), megakaryocyte derived growth factor (MGDF), keratinocyte growth factor (KGF), platelet-derived growth factor (PGDF), novel erythropoiesis stimulating protein (NESP), bone morphogenetic protein (BMP), superoxide dismutase (SOD), tissue plasminogen activator (TPA), pro-urokinase, urokinase, streptokinase, kallikrein, a protease inhibitor e.g. aprotinin, an enzyme such as asparaginase, arginase, arginine deaminase, adenosine deaminase, ribonuclease, catalase, uricase, bilirubin oxidase, trypsin, papain, alkaline phosphatase, glucoronidase, purine nucleoside phosphorylase or batroxobin, an opioid, e.g. endorphins, enkephalins or non-natural opioids, a neuropeptide, neuropeptide Y, calcitonin, cholecystokinins, corticotrophin-releasing factor, vasopressin, oxytocin, antidiuretic hormones, thyrotropin releasing hormone, relaxin, peptideYY, pancreastic polypeptide, CART (cocaine and amphetamine regulated transcript), a CART related peptide, perilipin, melanocortins (melanocyte-stimulating hormones) such as MSH, melanin-concentrating hormones, natriuretic peptides, adrenomedullin, endothelin, secretin, amylin, vasoactive intestinal peptide (VIP), pituary adenylate cyclase activating polypeptide (PACAP), bombesin, bombesin-like peptides, thymosin, heparin-binding protein, soluble CD4, hypothalmic releasing factor, melanotonins, and human antibodies and humanized antibodies, and other pharmaceutical compositions suitable for administration with the delivery devices described herein. The term proteins, as used herein, includes peptides, polypeptides, consensus molecules, analogs, derivatives or combinations thereof.

The pharmaceutical compositions also may include therapeutic and pharmaceutic agents such as, but not limited to: antiproliferative/antimitotic agents including natural products such as *Vinca* alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which don't have the capacity to synthesize their own asparagine); antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine{cladribine}); platinum coordination complexes (cisplatin, carboplatin), procarbazine, hydroxyurea, mitotane, aminoglutethimide; hormones (i.e. estrogen); Anticoaglants (heparin, synthetic heparin salts and other inhibitors of thrombin); fibrinolytic agents (such as tissue plasminogen activator, streptokinase and urokinase); antiplatelet (aspirin, dipyridamole, ticlopidine, clopidogrel, abciximab); antimigratory; antisecretory (breveldin); antiinflammatory: such as adrenocortical steroids (cortisol, cortisone, fludrocortisone, prednisone, prednisolone, 6a-methylprednisolone, triamcinolone, betamethasone, and dexamethasone), non-steroidal agents (salicylic acid derivatives i.e. aspirin; para-aminophenol derivatives i.e. acetominophen; Indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressive: (cyclosporine, tacrolimus (FK-506), sirolimus (rapamycin), azathioprine, mycophenolate mofetil); nitric oxide donors; anti-sense olgio nucleotides and combinations thereof.

The pharmaceutical compositions include any extended half-life variants of active ingredients contained therein or analogues thereof. Thus, the active ingredients can be any long acting variants of the active ingredient listed herein or analogues thereof. In some embodiments, the active ingredient includes any extended half-life or long acting variants of hGH, insulin, glucagon, glucagons-like peptide 1 (GLP-1), glucagons-like peptide 2 (GLP-2), insulin-like growth factors (IGFs). In some embodiments, the active ingredient is an extended half-life or long acting variant of hGH. Examples of extended half-life or long acting variants of hGH include, but are not limited to LB03002, NNC126-0883, NNC0195-0092, MOD-4023, ACP-001, Albutropin, somavaratan (VRS-317), and profuse GH.

Another aspect of this invention is directed to one or more of the medicaments, including one or more pharmaceutical compositions, as described above for subcutaneous injection or infusion, disposed within the medicament delivery devices described herein for the delivery of the medicament from a cartridge into an injection site through a cannula. Additionally, this invention contemplates methods of administering one or more of the medicaments, including pharmaceutical compositions, to patients with conditions susceptible to treatment with the medicaments, as well as methods of treating those conditions, by delivering the appropriate medicament using the delivery devices described herein.

Embodiments of the present invention will now be described, by way of example only, with reference to the accompanying drawings, in which like reference numerals are used for like features, and in which:

FIGS. 1(a) and 1(b) are cross-sectional views in perpendicular planes of a device according to a first embodiment of the present invention, when in an initial state;

FIG. 2 is a cut-away isometric view of the delivery device of FIG. 1, when in the initial state;

FIG. 3 is a cut-away isometric view of a control part of the delivery device of FIG. 1;

FIG. 4 is a cut-away isometric view of the delivery device of FIG. 1 after removal of a cap part;

FIG. 5 is a cut-away isometric view of the delivery device of FIG. 1 after an activation step has been performed;

Figure 6A:
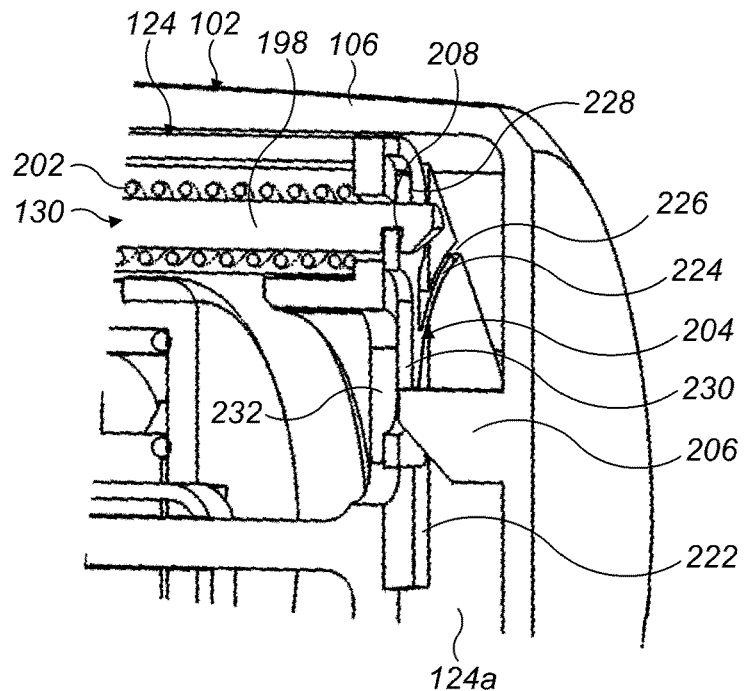
FIG. 6(a) is a cut-away isometric view of a proximal end part of the delivery device of FIG. 1 before the activation step has been performed.
Figure 6B:
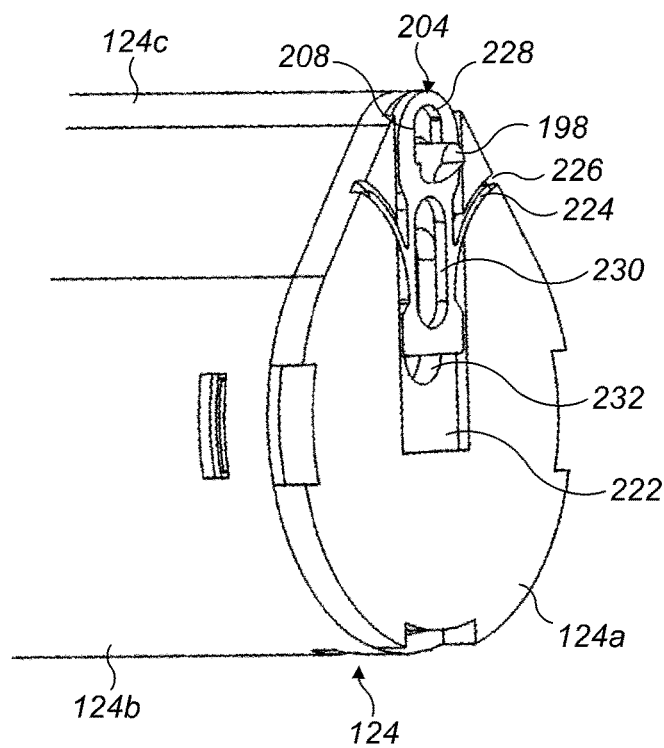
FIG. 6(b) is an isometric view of the proximal end part with a chassis component omitted for clarity.
Figure 7A:
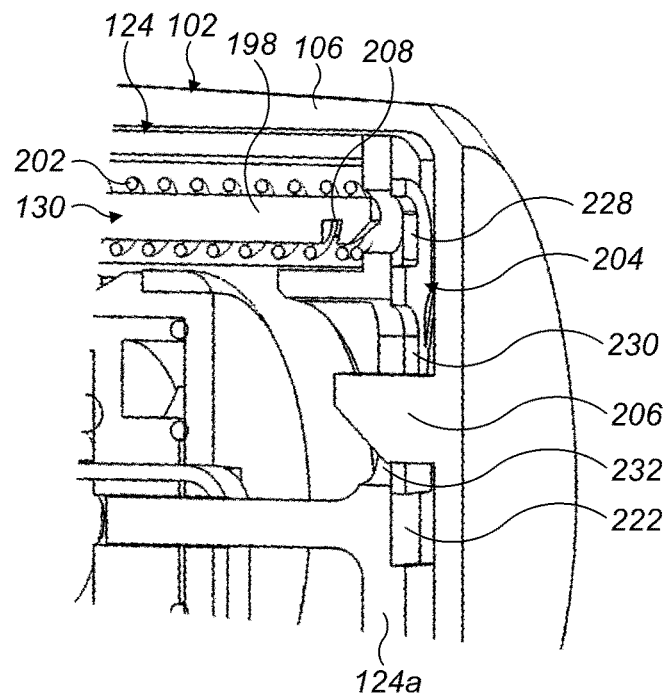
Figure 7B:
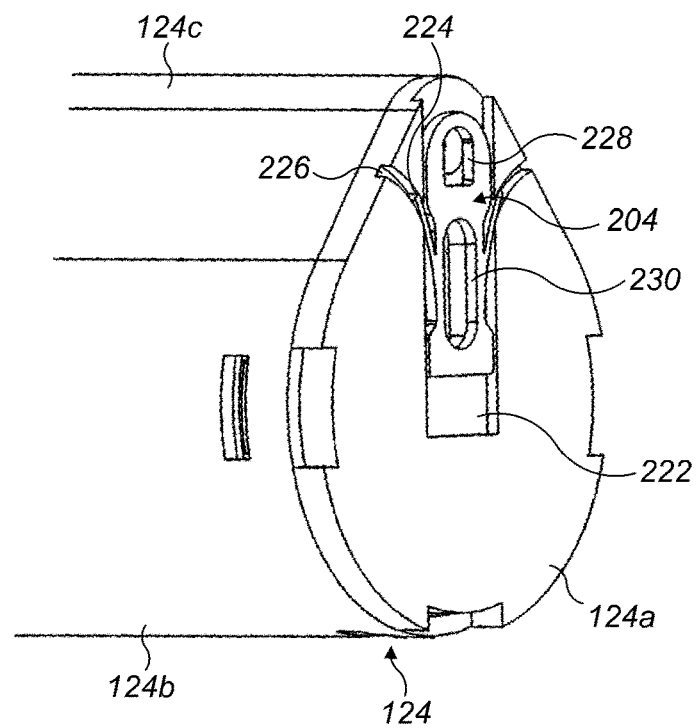
Figure 8A:
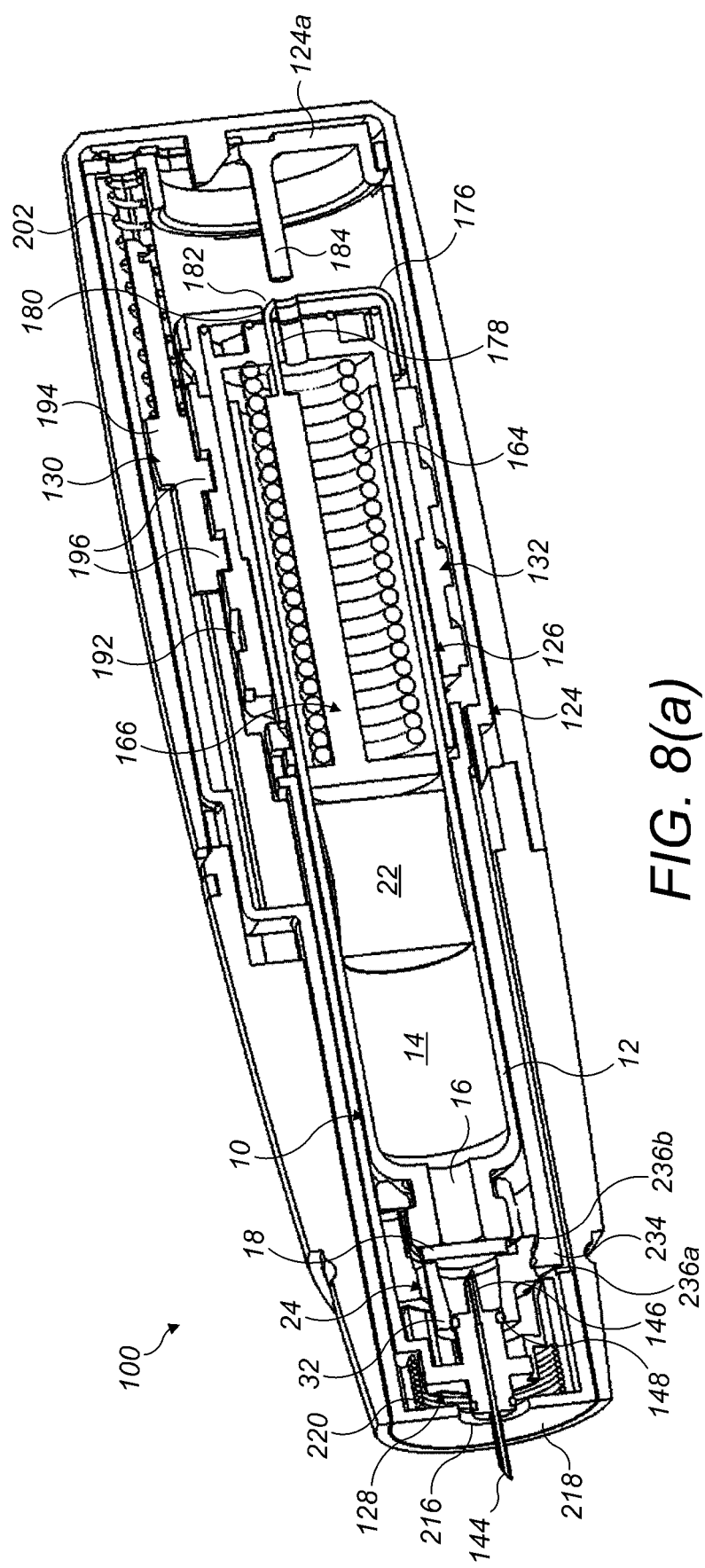
Figure 8B:
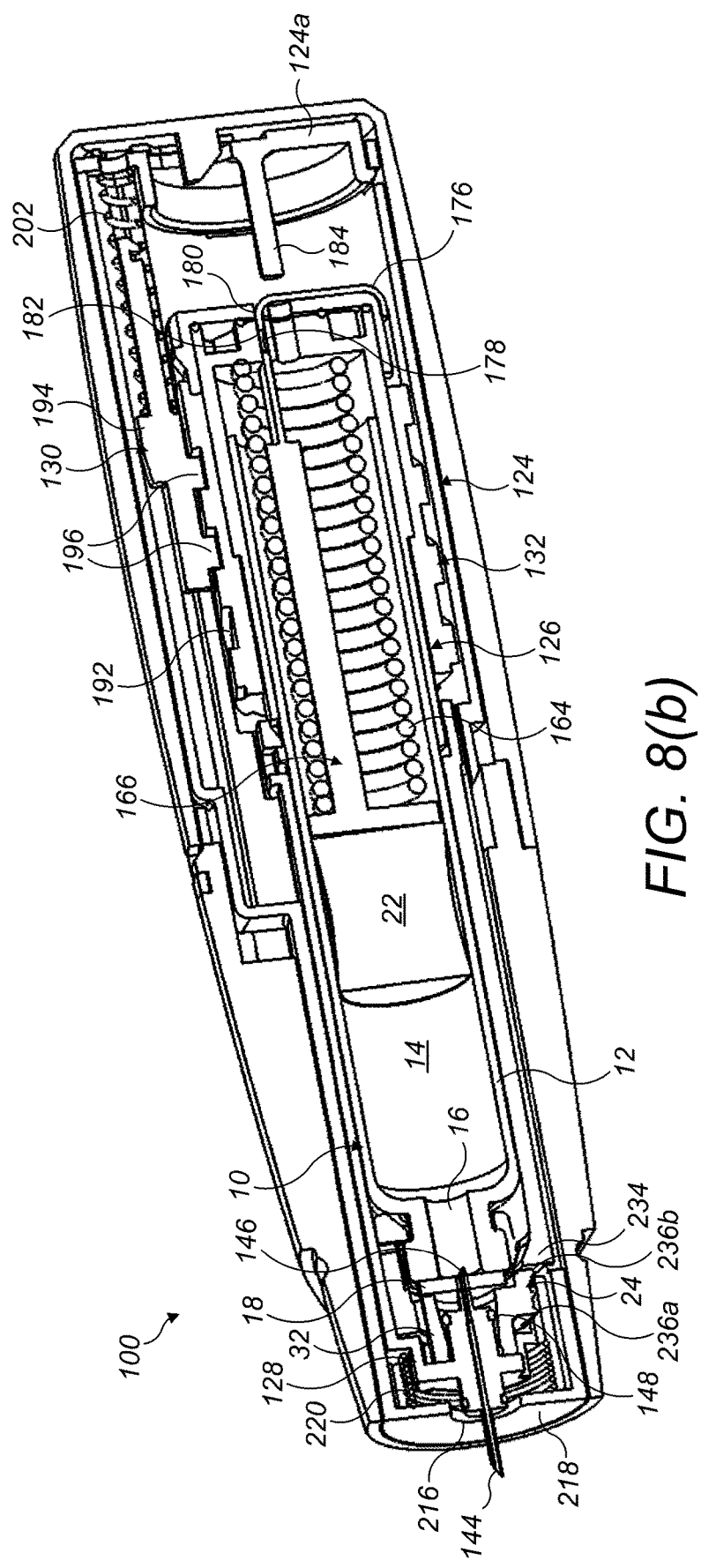
Figure 9A:
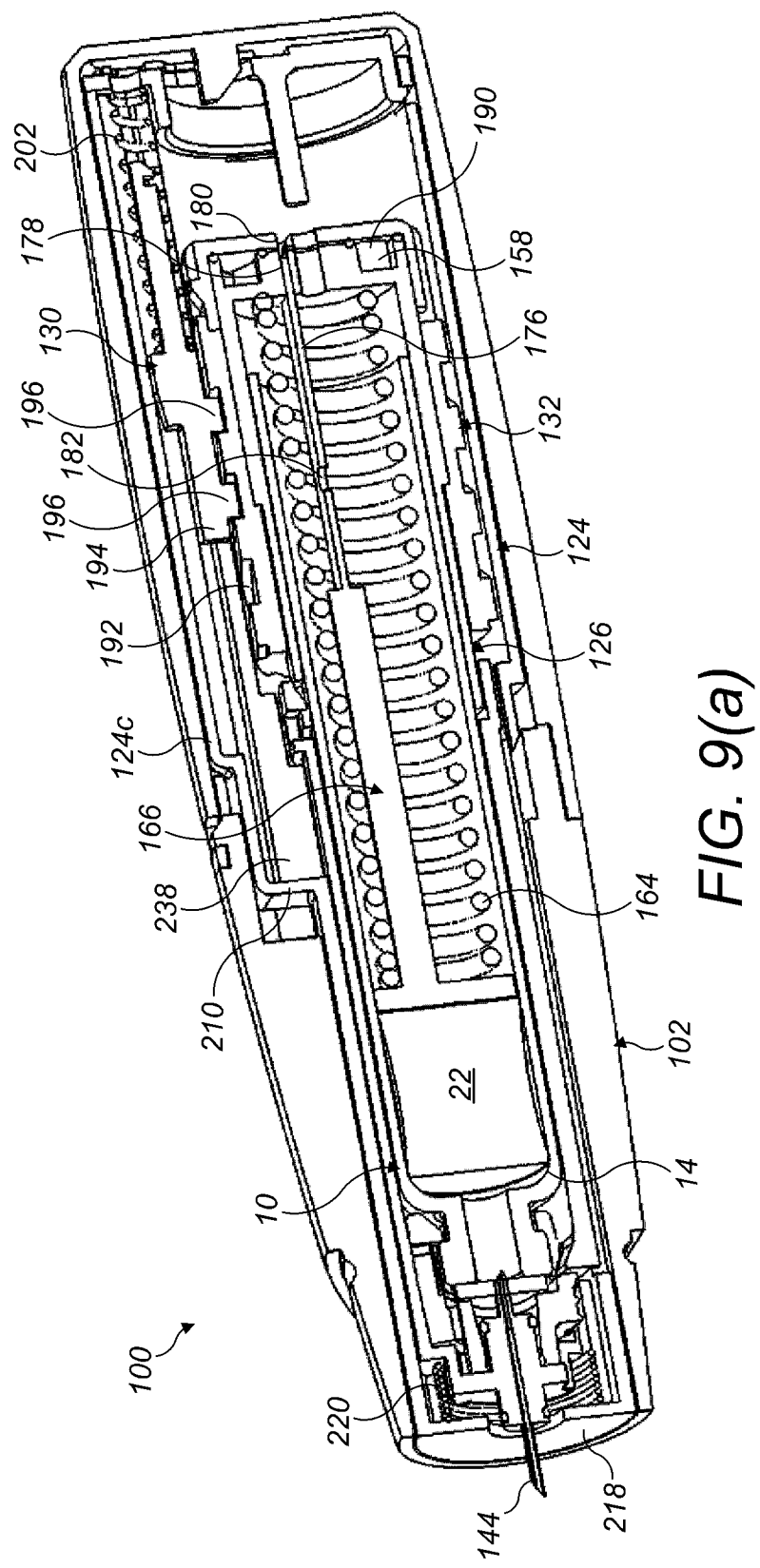
Figure 9B:
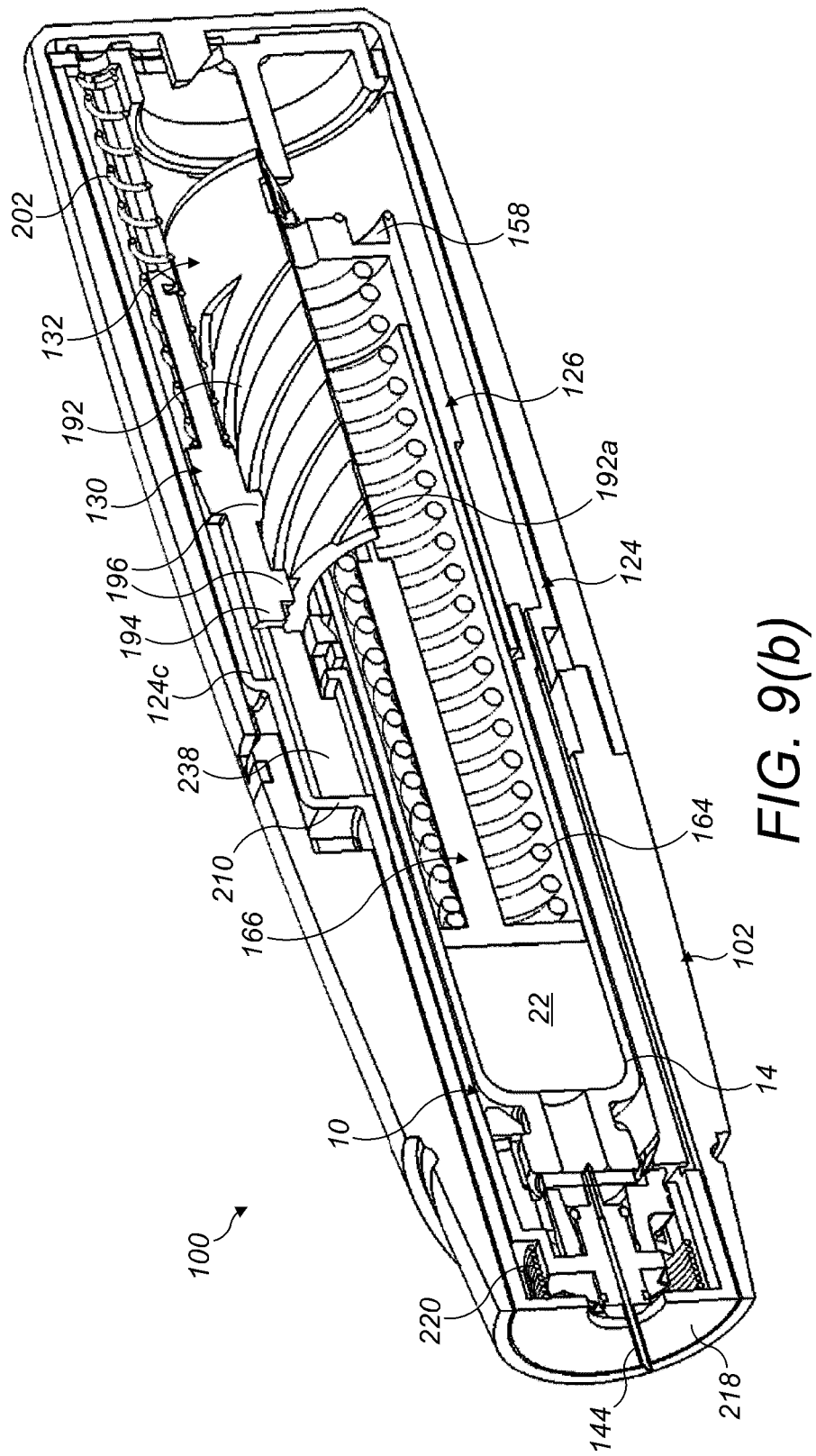
Figure 10:
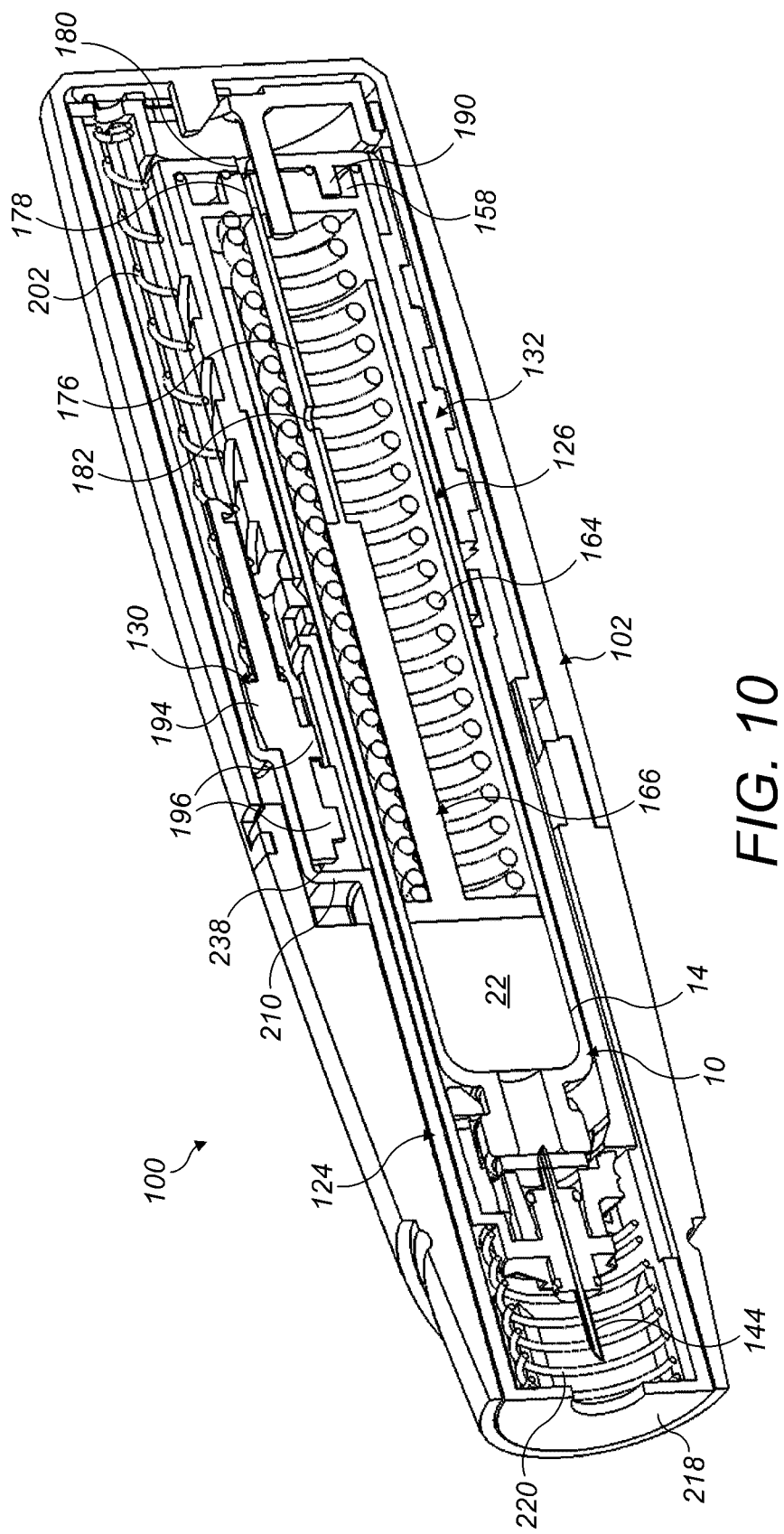
Figure 11:
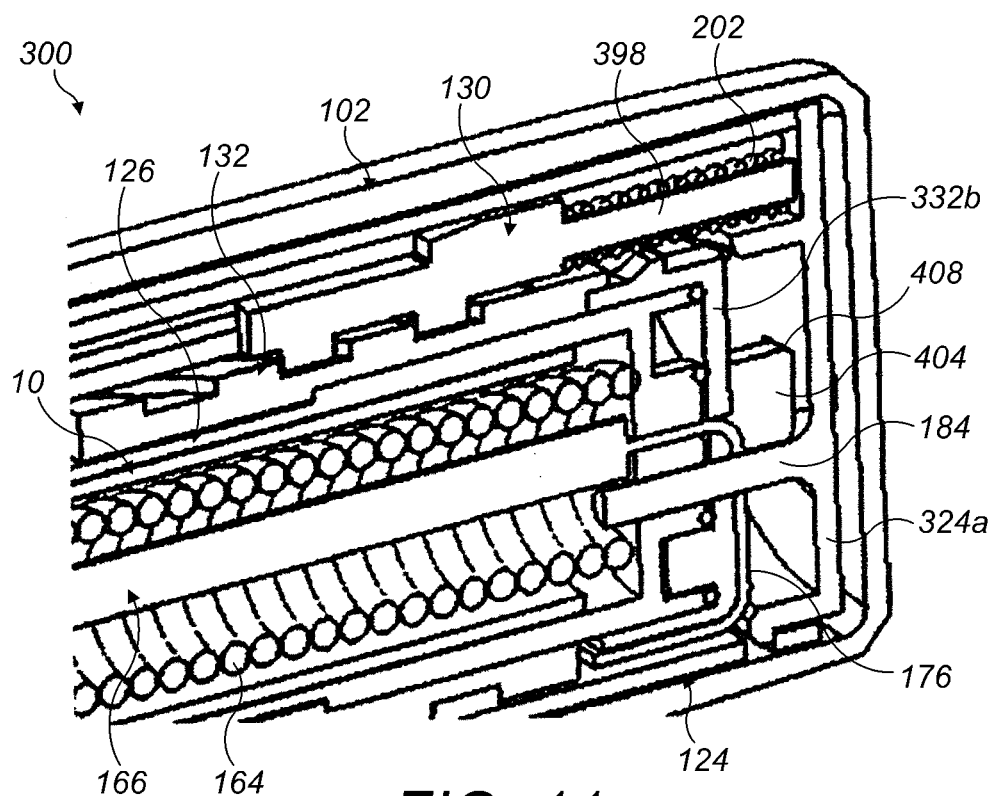
Figure 12:
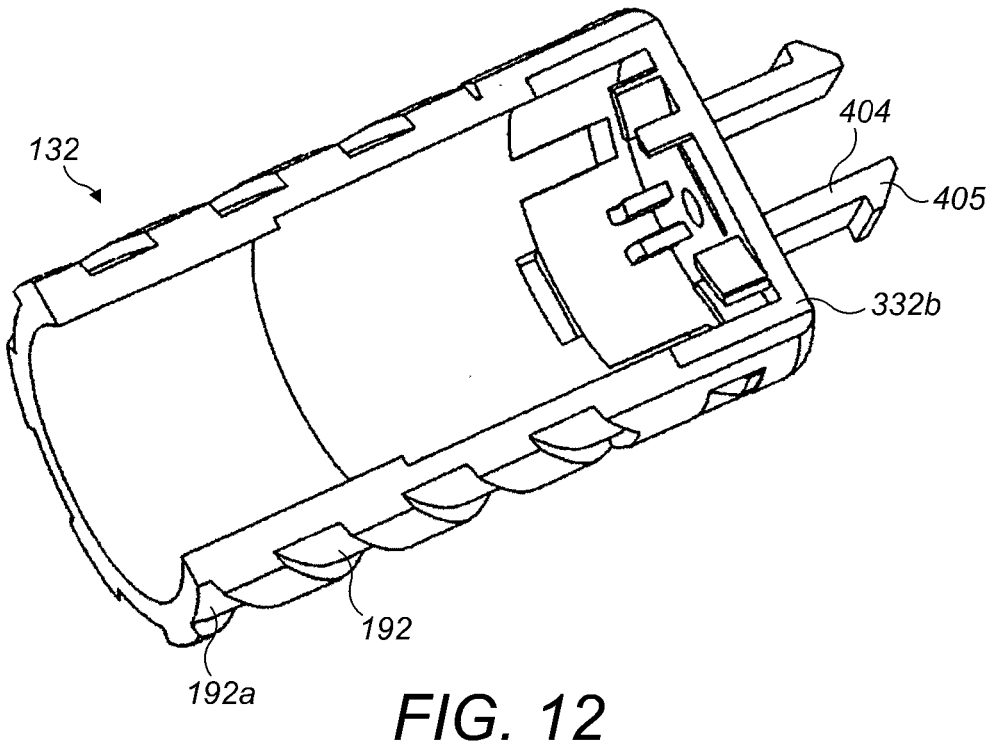
Figure 13A:
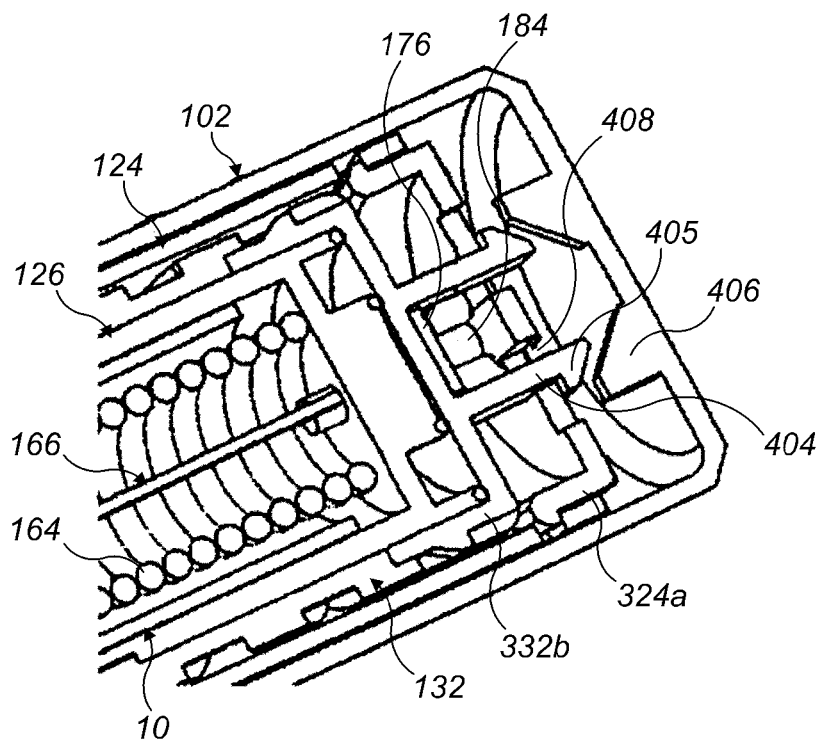
Figure 14:
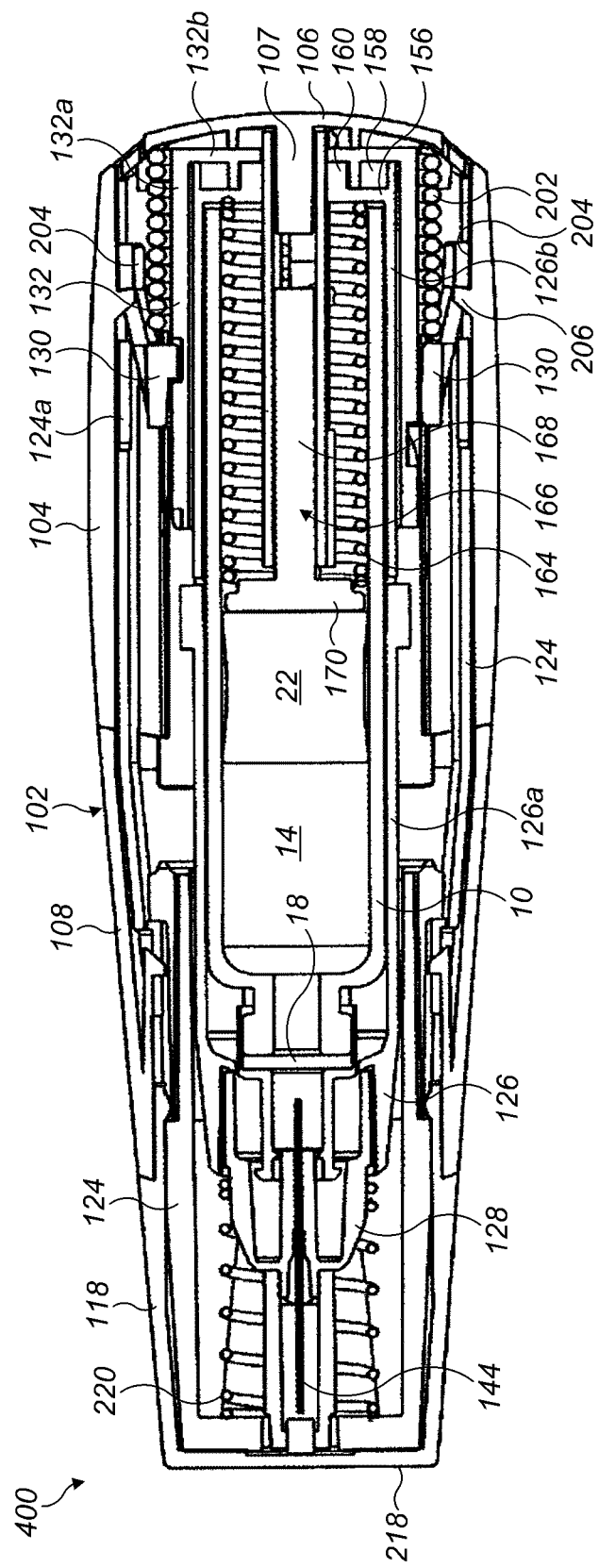
Figure 15:
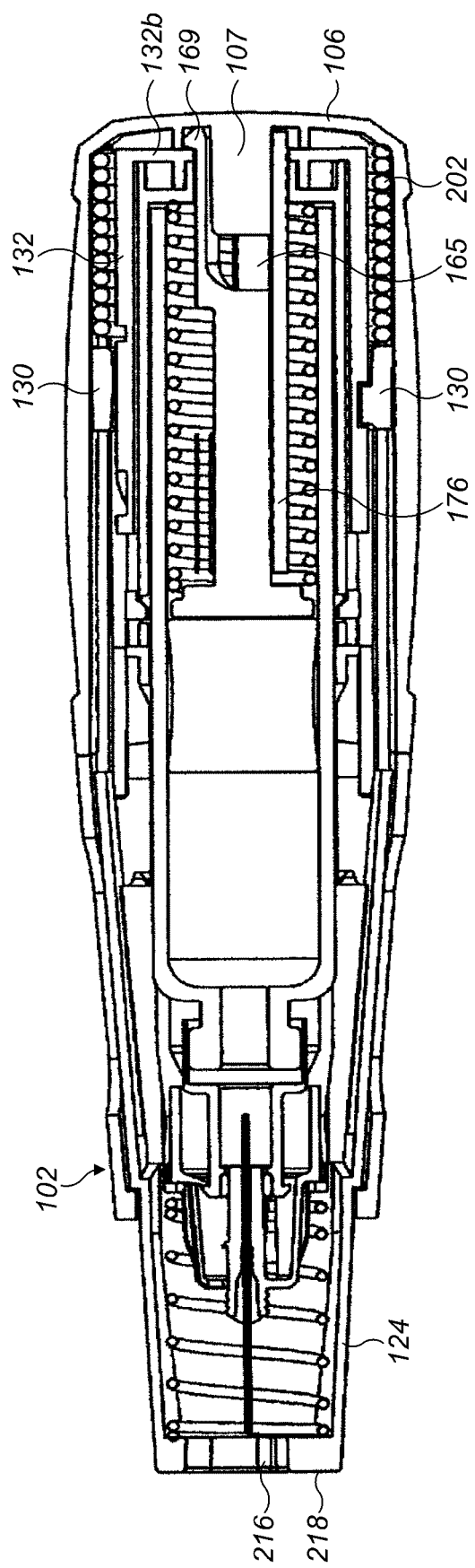
Figure 16:
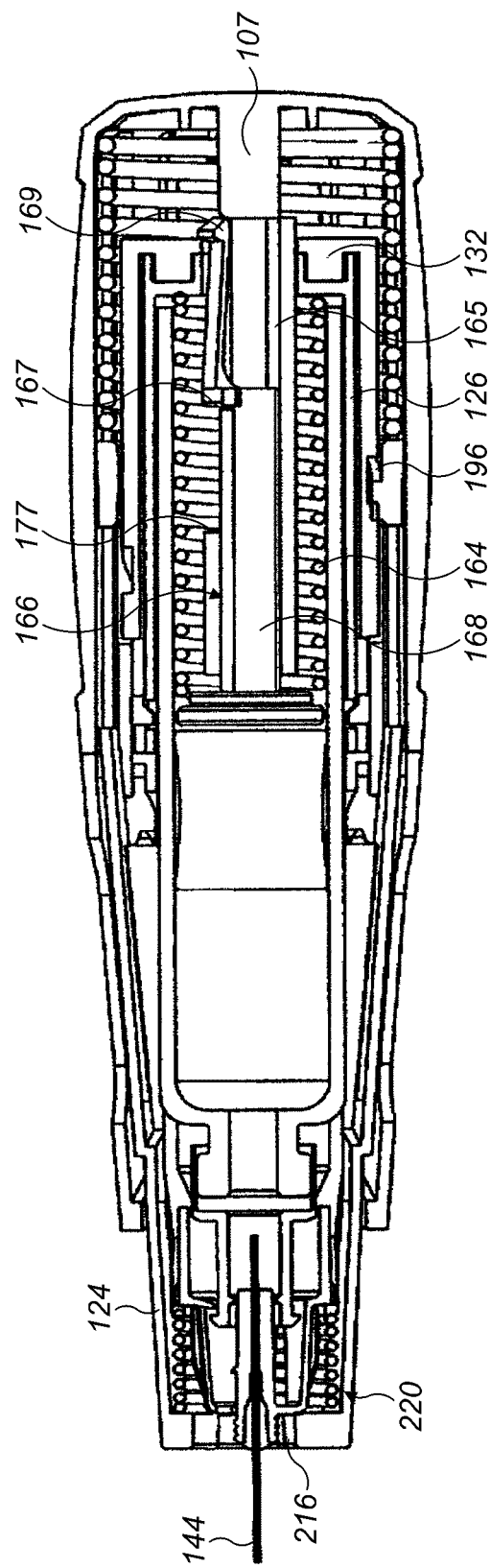
Figure 17:
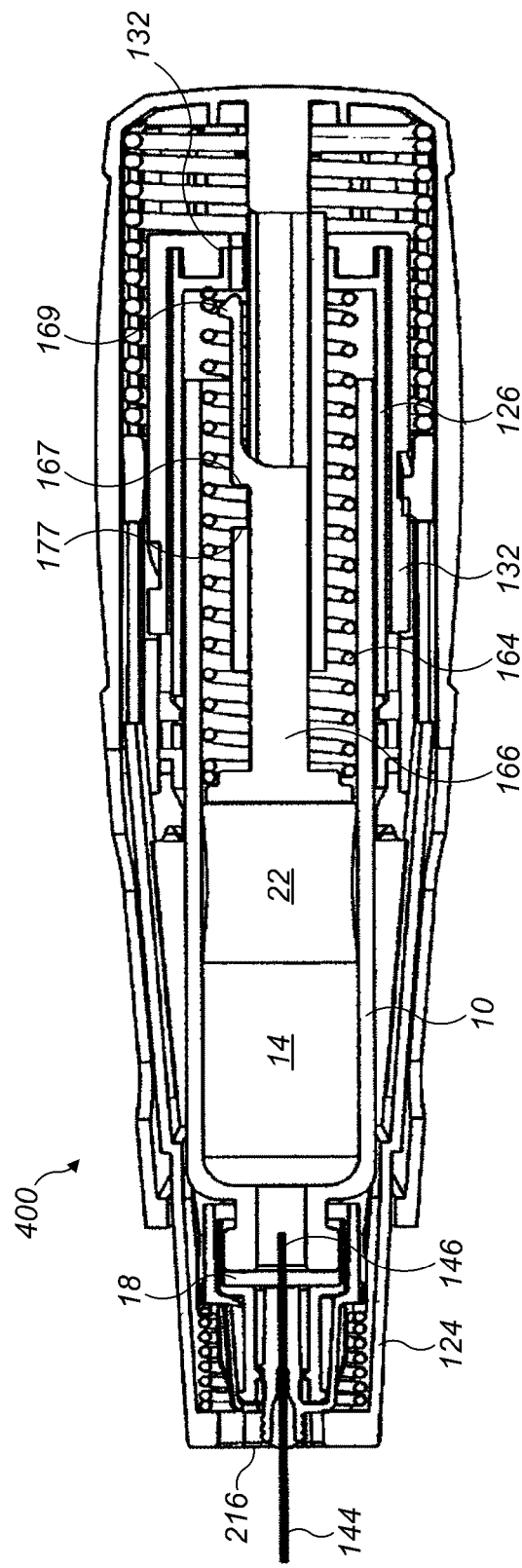
Figure 18:
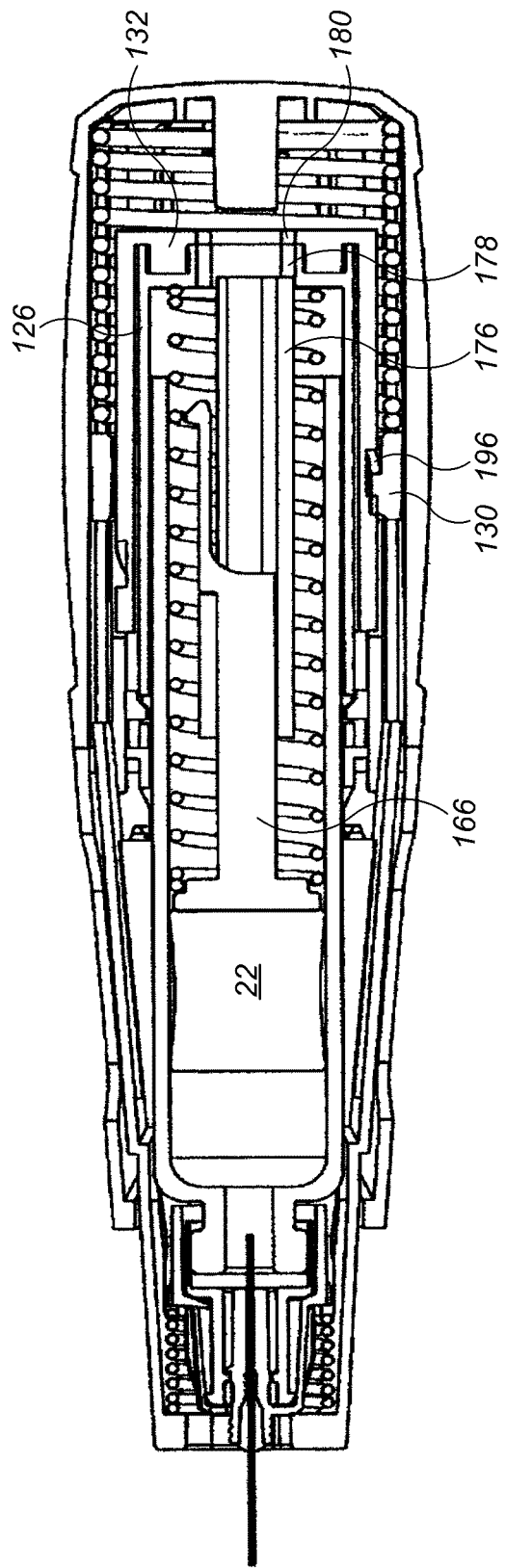
Figure 19:
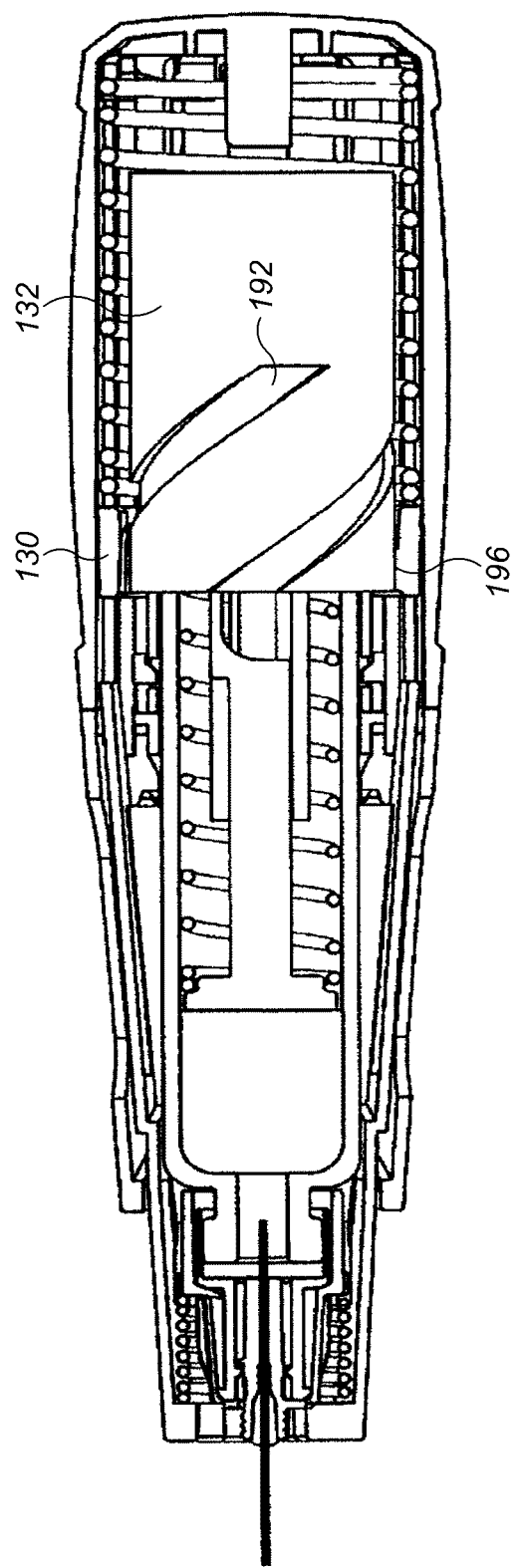
Figure 20:
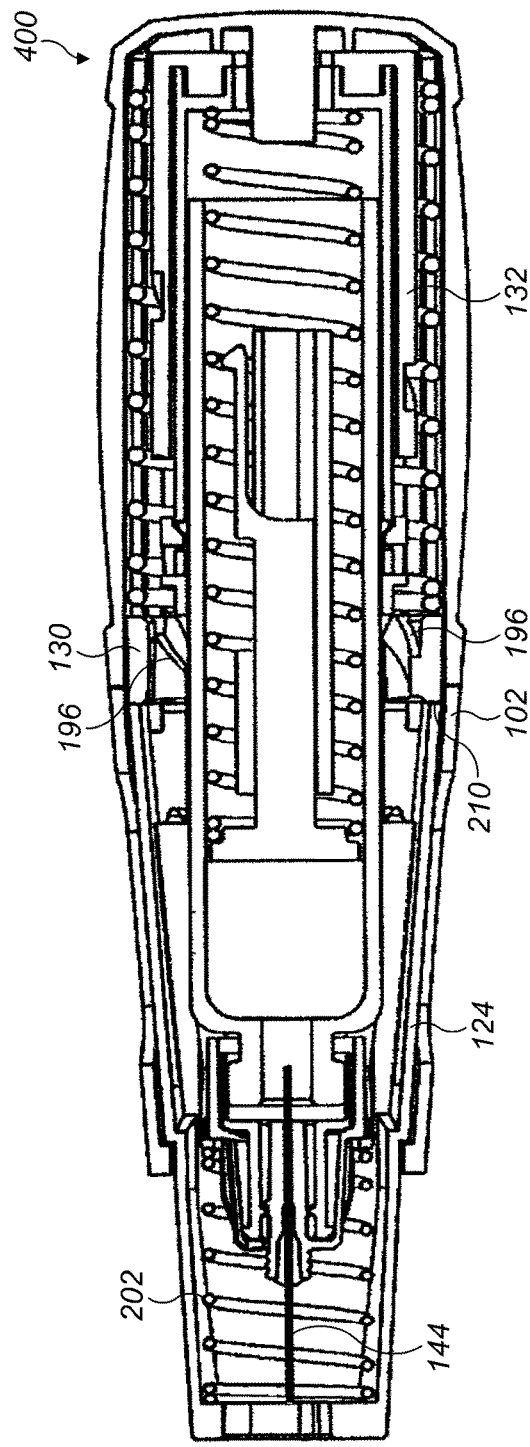
Figure 21:
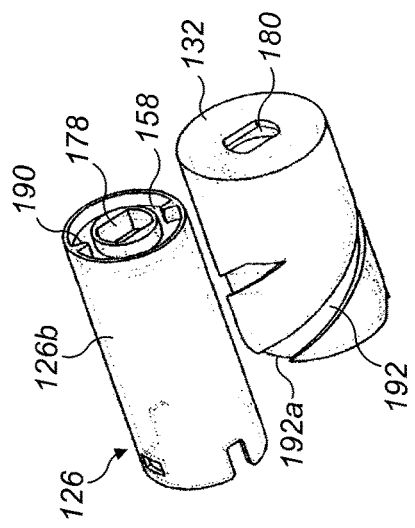
Figure 22:
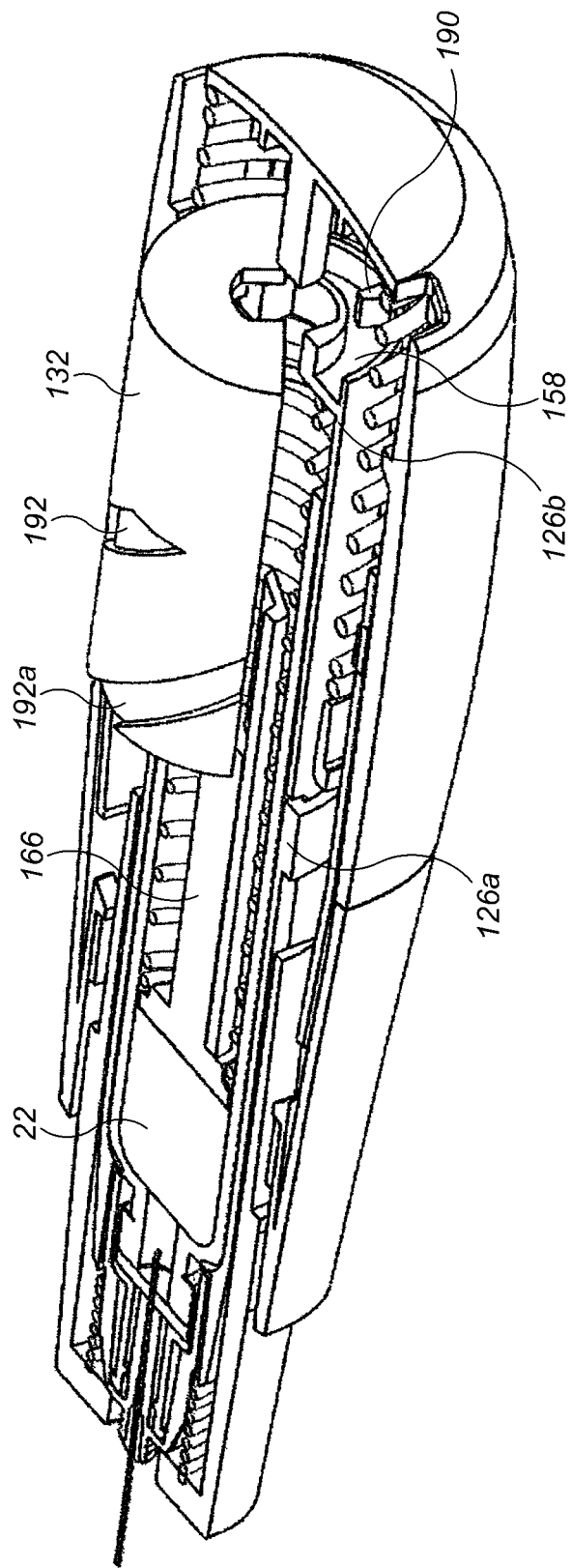
Figure 23A:
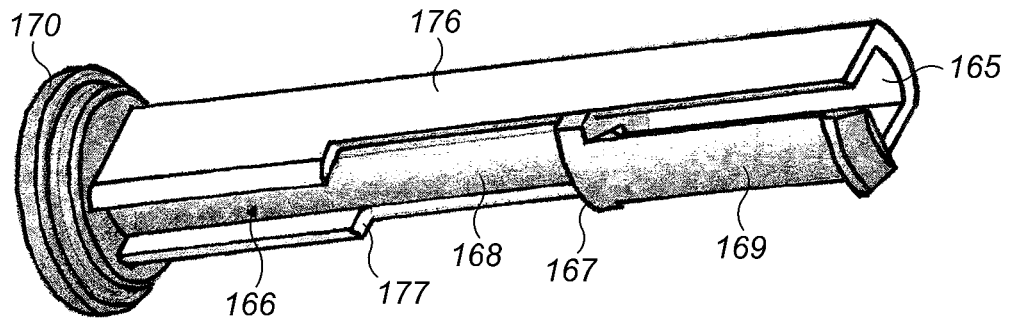
Figure 23B:
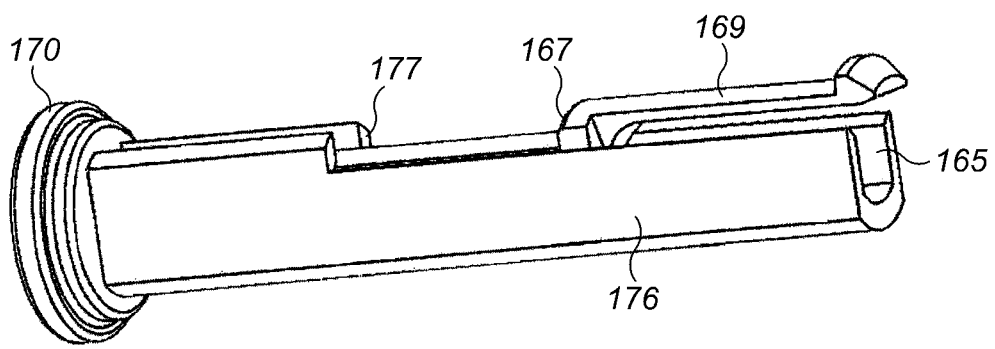
Figure 24:
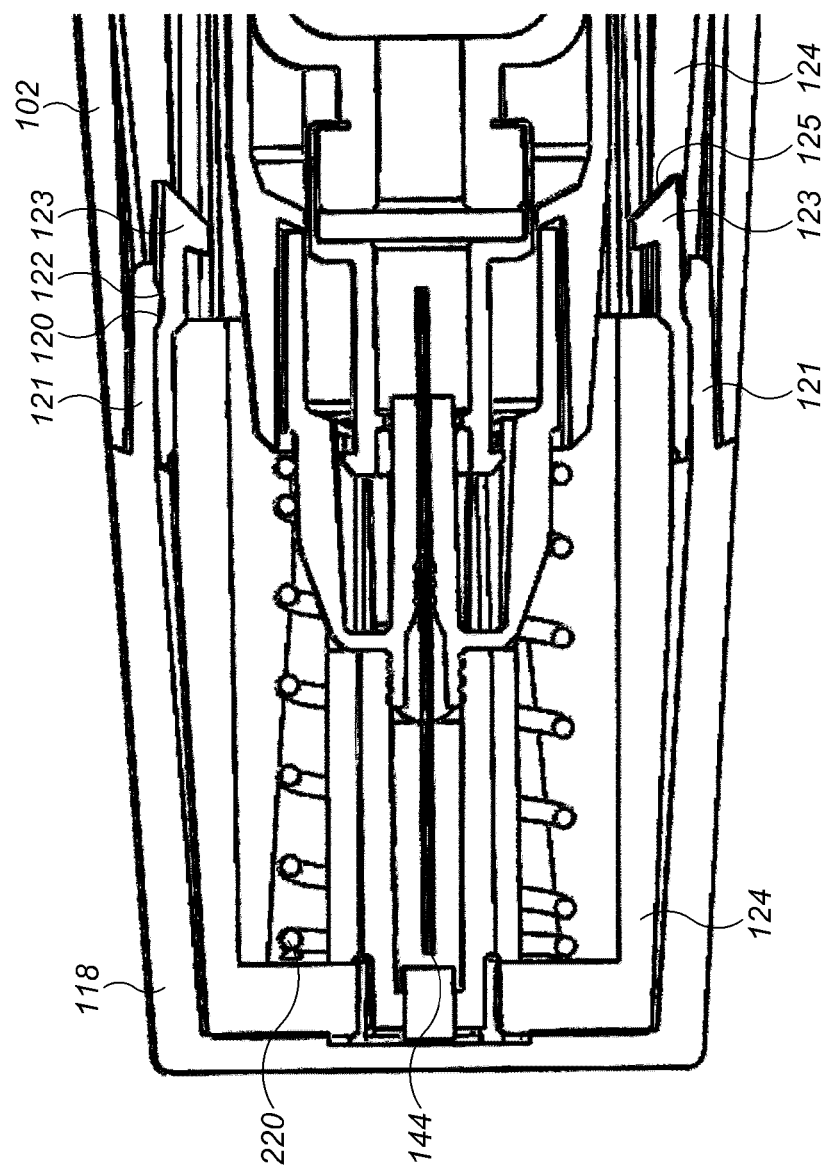
Figure 25:
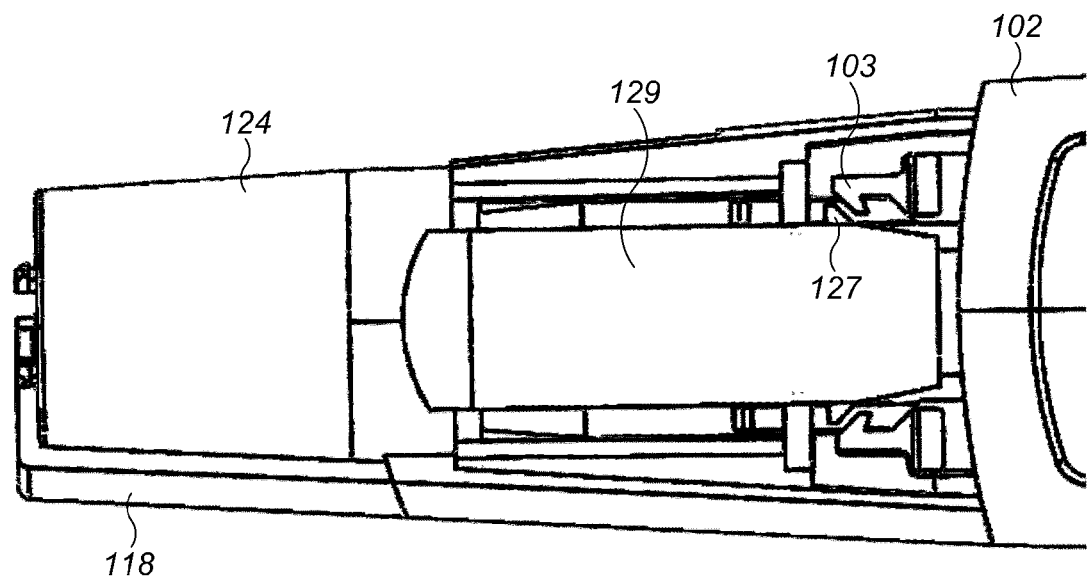
Figure 26:
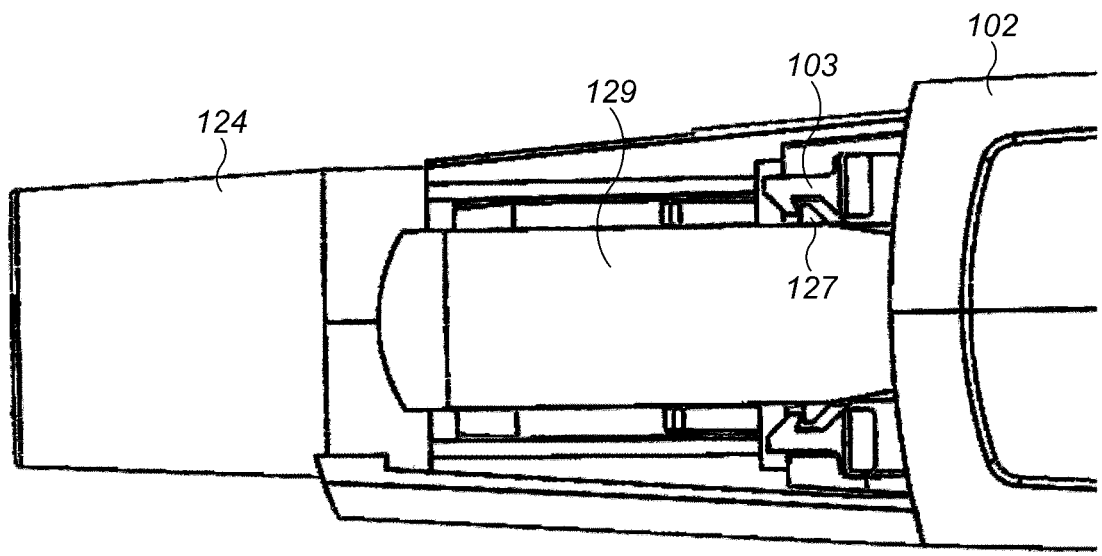

FIGS. 7(a) and 7(b) show the same views as FIGS. 6(a) and 6(b), after the activation step has been performed;

FIGS. 8(a) and 8(b) are cut-away isometric views of the delivery device of FIG. 1 showing sequential stages of operation at the end of an insertion stroke of the device;

FIGS. 9(a) and 9(b) are cut-away isometric views of the delivery device of FIG. 1 showing sequential stages of operation at the end of a delivery stroke of the device;

FIG. 10 is a cut-away isometric view of the delivery device of FIG. 1 at the end of a retraction stroke of the device;

FIG. 11 is a cut-away isometric view of a proximal end part of a delivery device according to a second embodiment of the invention;

FIG. 12 is a cut-away isometric view of a control part of the delivery device of FIG. 11;

FIGS. 13(a), (b), (c) and (d) are cut-away isometric views of the proximal end part of the delivery device of FIG. 11 showing sequential stages of operation during an activation step of the device;

FIG. 14 is a cross-sectional view through the widest plane of a device according to a third embodiment of the present invention, when in an initial state;

FIG. 15 is a cross-sectional view through the narrowest plane of the device of FIG. 14, in an initial state after removal of a cap part;

FIG. 16 is a cross-sectional view through the narrowest plane of the device of FIG. 14, during the insertion stroke of the device;

FIG. 17 is a cross-sectional view through the narrowest plane of the device of FIG. 14, at the end of an insertion stroke of the device;

FIG. 18 is a cross-sectional view through the narrowest plane of the device of FIG. 14, during the delivery stroke of the device;

FIG. 19 is a cross-sectional view through the narrowest plane of the device of FIG. 14, at the end of the delivery stroke of the device, with the control sleeve shown;

FIG. 20 is a cross-sectional view through the narrowest plane of the device of FIG. 14, at the end of the retraction stroke of the device;

FIG. 21 is an isometric view of a proximal carrier part and a control sleeve part of the delivery device of FIG. 14;

FIG. 22 is a cut-away isometric view of the delivery device of FIG. 14, at the end of the delivery stroke of the device;

FIGS. 23(a), (b), and (c) are isometric views of a drive element plunger part of the delivery device of FIG. 14;

FIG. 24 shows a cross sectional view of a distal end part of a delivery device according to a fourth embodiment of the present invention in which an alternative cap arrangement is provided;

FIG. 25 shows a cross sectional view of a distal end part of a delivery device according to a fifth embodiment of the present invention in which a chassis locking mechanism is provided; and FIG. 26 shows a cross sectional view of the distal end part of the delivery device shown in FIG. 26 after the chassis locking mechanism has locked the chassis to the casing.

Figure 1A:
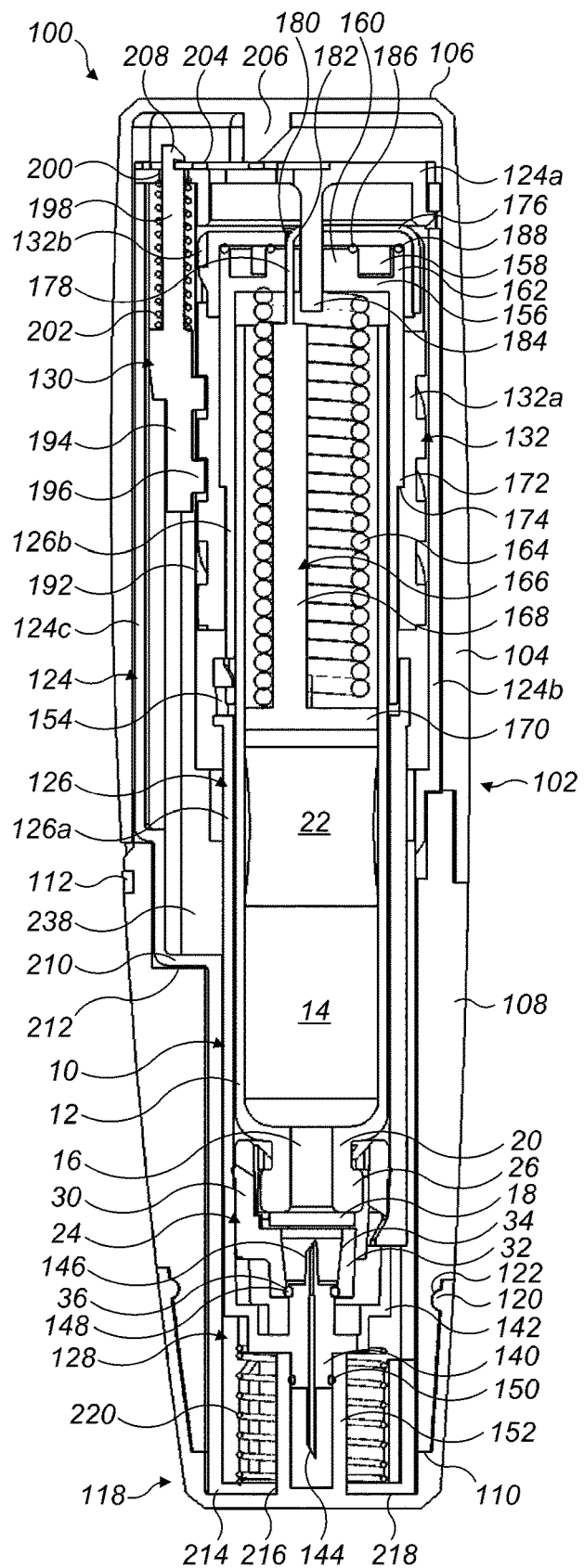
Figure 1B:
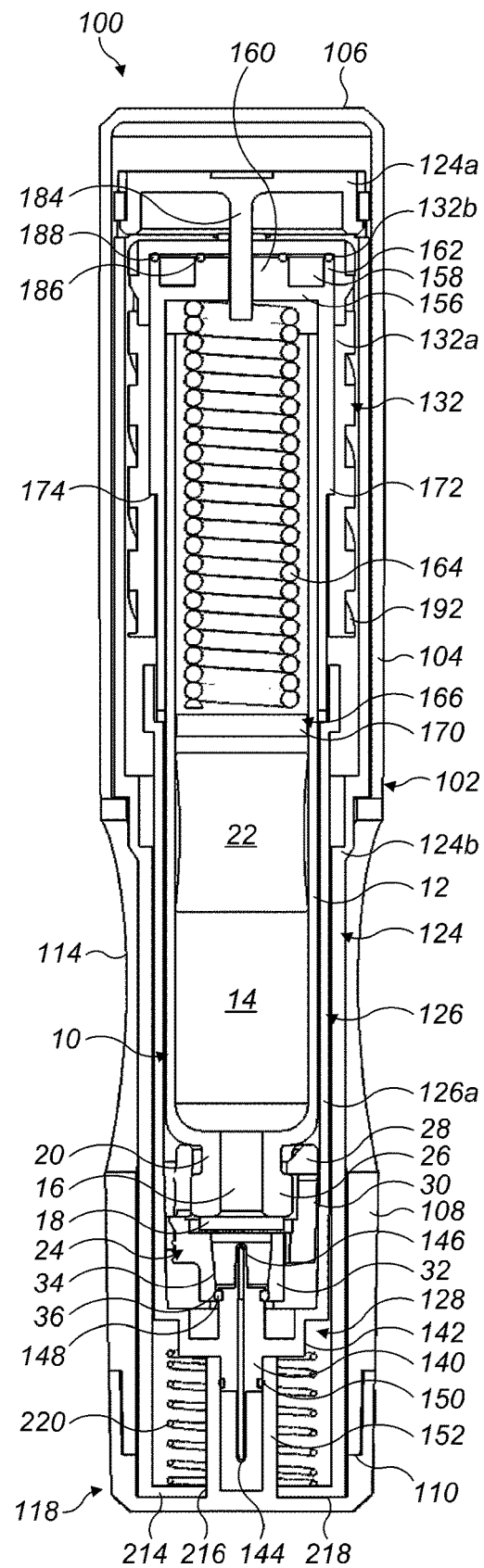

Throughout this description, the term "distal" and related terms are used to refer to the end of the device that is placed against the injection site, in use (i.e. the lower end of the device in the orientation shown in FIGS. 1(a) and 1(b)). The term "proximal" and related terms are used to refer to the opposite end of the device, furthest from the injection site in use (i.e. the upper end of the device in the orientation shown in FIGS. 1(a) and 1(b)).

FIGS. 1 and 2 show a first embodiment of a medicament delivery device 100, when in an initial state. The device 100 is arranged to deliver a single dose of a medicament from a medicament cartridge 10.

The device 100 comprises an elongate, two-part housing or casing 102. The casing 102 comprises a proximal casing part 104 with a closed proximal end 106, and a distal casing part 108 with an open distal end 110. The two casing parts 104, 108 are attached to one another by a clipping arrangement 112 during assembly of the device. A pair of windows 114, visible in FIG. 1(b), are provided in the distal casing part 108 to provide visibility of the cartridge 10.

A removable cap 118 is provided to close the distal end 110 of the casing 102. As seen most clearly in FIGS. 1(a) and 2, the cap 118 is generally cup-shaped and includes ridge formations 120 that engage with corresponding grooves 122 in a recessed distal end part of the casing 102 to provide a degree of resistance to removal of the cap 118 from the casing 102.

The casing 102 houses a chassis 124, a generally tubular cartridge carrier 126 having a needle assembly 128 at its distal end, and the medicament cartridge 10. These components are arranged concentrically, with the cartridge 10 being received in the carrier 126, the carrier 126 being received in the chassis 124 and the chassis being received in the casing 102. The casing 102 also houses a control arrangement comprising a coupling member in the form of a control pin 130 and a control part or control sleeve 132 that is arranged concentrically around a proximal part of the carrier 126.

The cartridge 10 comprises a generally tubular body 12 which defines a chamber 14 for containing a medicament substance. A distal end of the body 12 defines an outlet 16 of the chamber 14 that is closed by a closure member in the form of an elastomeric disc or septum 18, which seals against the end face of a reduced-diameter neck 20 of the body 12. A piston member or stopper 22 is received in the proximal end of the body 12 to close the second end of the chamber 14, so that the medicament substance is contained between the septum 18 and the stopper 22.

The septum 18 is held in place by a coupling element 24 that is in clipped engagement with a collar 26 on the neck 20 of the body 12 by way of clip formations 28 (one of which can be seen in FIG. 1(b)). The clip formations 28 are disposed at the ends of a plurality of legs 30 that extend proximally from a tubular throat 32 of the coupling element 24. The legs 30 are held in place by a tubular distal part 126a of the carrier 126, which therefore serves to clamp the coupling element 24 to the neck 20 of the body 12.

The throat 32 defines a generally frustoconical bore 34. An inner end of the throat 32 presses against the septum 18 to seal the septum 18 against the end of the neck 20. An annular groove 36 is disposed on the inside of the bore 34 adjacent to the distal end of the throat 32.

The needle assembly 128 of the cartridge carrier 126 comprises a tubular holder 140 that is held in a coaxial arrangement with the distal part 126a of the carrier 126 by a plurality of arms 142. A cannula, comprising a hypodermic needle 144, extends distally from the holder 140. An internal piercing member 146, in the form of a second needle, projects proximally from the holder 140 towards the container 10. The piercing member 146 is tubular, and the bore of the piercing member 146 is in fluid communication with the lumen of the needle 144. A first O-ring 148 is retained in an annular recess on the outer wall of the holder 140 close to its proximal end. When the device 100 is in the initial state, as shown in FIGS. 1 and 2, the carrier 126 and the container 10 are arranged in a first attachment position relative to one another. In this first attachment position, the first O-ring 148 locates in the annular groove 36 of the throat 32 of the container coupling element 24 and the piercing member 172 does not pierce the septum 18, so that the outlet 16 of the container 10 remains closed. The coupling element 24 is shaped to cooperate with the arms 142 of the needle assembly 128 to prevent rotation of the cartridge 10 with respect to the carrier 126.

A second O-ring 150 is retained in a further annular recess on the outer wall of the holder 140, adjacent to the distal end of the holder 140. With the cap 118 in place, the distal end of the needle 144 is received in the bore of an internal tubular extension 152 of the cap 118, and the second O-ring 150 forms a seal between the tubular extension 152 of the cap 118 and the holder 140. In this way, with the cap 118 in place and the device 100 in the initial state, the first and second O-rings 148, 150 form seals to preserve the sterility of the needle 144, the piercing member 146 and the fluid flow route therebetween.

The needle assembly 128 is disposed at a distal end of the distal part 126a of the cartridge carrier 126. During assembly of the device 100, a proximal part 126b of the carrier 126 is connected to the distal part 126a by a clipping arrangement 154 to enclose the cartridge 10 in the carrier 126. The proximal end of the proximal carrier part 126b is closed by an end wall 156. An annular recess 158 is formed in the proximal side of the end wall 156, defining a central land 160 and a peripheral lip 162.

The carrier 126 also houses a drive spring 164, in the form of a compression spring, and a drive element plunger 166, which is arranged to cooperate with the stopper 22 of the cartridge 10 to drive the stopper 22 in the distal direction during a delivery stroke of the device 100. The drive spring 164 is initially compressed and is arranged concentrically around a shaft part 168 of the plunger 166 (the shaft part 168 is not visible in FIG. 1(b)). The distal side of the carrier end wall 156 forms a spring seat for the proximal end of the drive spring 166. A distal end of the drive spring 166 bears against a disc-shaped head part 170 of the plunger 166.

The control sleeve 132 comprises a tubular body 132a and a cap part 132b that is clipped to the body 132a. The cap part 132b bears against the distal end of the cartridge carrier 126 to prevent distal movement of the control sleeve 132 relative to the carrier 126. Referring additionally to FIG. 3, the inner wall of the control sleeve body 132a includes a distally-facing shoulder 172 that cooperates with a corresponding proximally-facing shoulder 174 formed on the outer wall of the proximal carrier part 126b to prevent proximal movement of the control sleeve 132 relative to the carrier 126. In this way, the control sleeve 132 can rotate with respect to the carrier 126, but axial movement between the control sleeve 132 and the carrier 126 is prevented.

As shown in FIGS. 1(a) and 2, a locking element, comprising an elongate flexible strip 176, extends from the proximal end of the plunger shaft 168 and passes through a first opening or slot 178 formed in the central land 160 of the carrier end wall 156 and through a second opening or slot 180 formed in the cap part 132b of the control sleeve 132. The locking strip 176 is initially in a storage configuration, in which the strip 176 is folded to extend laterally over the proximal end of the control sleeve 132 and then distally along the side of the cap part 132b of the control sleeve 132. In the initial state of the device, the locking strip 176 keeps the slots 178, 180 in alignment so that relative rotation between the control sleeve 132 and the carrier 126 is prevented.

The locking strip 176 also serves to prevent release of the drive spring 164 from its initial compressed configuration. To this end, an aperture 182 is provided in the laterally-extending region of the locking strip 176. A retaining member or pin 184 extends distally from a proximal end cap 124a of the chassis 124 to pass through the aperture 182 in the locking strip 176, and through further holes formed in the cap part 132b of the control sleeve 132 and in the central land 160 of the carrier end wall 156. In this way, in the initial state of the device 100, the retaining pin 184 holds the locking strip 176 in place with respect to the chassis 124, preventing distal movement of the plunger 166.

The control sleeve 132 and the carrier 126 cooperate to form a rotational damping arrangement. Accordingly, the cap part 132b of the control sleeve 132 closes the annular recess 158 in the carrier end wall 156 so that the recess 158 provides a damping chamber for containing a viscous substance, such as a silicone grease. An inner O-ring 186 and an outer O-ring 188 are disposed on the central land 160 and the peripheral lip 162 of the end wall 156 to seal the viscous substance in the recess 158. Each O-ring 186, 188 is seated in corresponding grooves on the carrier end wall 156 and the cap part 132b of the control sleeve 132. A plurality of vanes 190 (shown most clearly in FIG. 3) project distally from the cap part 132b of the control sleeve 132, into the recess 158, so that rotation of the control sleeve 132 with respect to the carrier 126 during operation of the device 100 causes the vanes 190 to move through the viscous substance, thereby damping the rotational movement, as will be explained in more detail below.

The outer wall of the control sleeve body 132a is provided with helical grooves or tracks 192 with open distal ends 192a (see FIG. 3). Referring again to FIGS. 1(a) and 2, in the initial state of the device 100, axial movement of the control sleeve 132 and the carrier 126 relative to the chassis 124 is prevented by engagement between the control pin 130 and the helical tracks 192. As can be seen most clearly in FIGS. 1(a) and 2, the control pin 130 extends parallel to the axis of the control sleeve 132, and includes a head part 194 having a pair of teeth 196 that engage with adjacent tracks 192 in the control sleeve body 132a. An elongate shaft 198 extends proximally from the head part 194 of the control pin 130 and passes through an aperture 200 in the chassis end cap 124a.

The control pin 130 is biased in the distal direction by an insertion spring 202, comprising a compression spring, which is disposed around the shaft 198 and acts between the chassis end cap 124a and the head part 194 of the control pin 130. In the initial state of the device 100, distal movement of the control pin 130 is prevented by a latch arrangement. The latch arrangement comprises a latch member 204 that is retained on the proximal side of the chassis cap 124a and a trigger ramp formation 206 that extends distally from the proximal end of the casing 102. As will be described in more detail below, prior to activation of the device 100, the latch member 204 is biased into engagement with a slot 208 in the shaft 198 of the control pin 130 to latch the control pin 130 to the chassis 124.

With the control pin 130 latched in position with respect to the chassis 124 and with rotation of the control sleeve 132 with respect to the carrier 126 prevented by the locking strip 176, the control sleeve 132 and hence the carrier 126 are held in the initial position until the device is activated, as will be explained later.

Referring still to FIGS. 1(a) and 2, the chassis 124 comprises a generally tubular body 124b that has an enlarged region 124c along part of one side to accommodate the control pin 130. The distal end of the enlarged region 124c of the chassis 124 provides a shoulder 210 that engages with a corresponding shoulder 212 of the casing, to block distal movement of the chassis 124 with respect to the casing 102. The proximal end cap 124a of the chassis 124 is clipped to the chassis body 124b during assembly of the device 100. The distal end of the chassis 124 is partially closed by an end wall 214, which includes a central aperture 216 to accommodate the tubular extension 152 of the cap 118, and a distal side of which provides a contact face 218 for contact with the injection site in use of the device 100. A retraction spring 220, in the form of a compression spring, is disposed between the end wall 214 of the chassis 124 and the distal end of the carrier 126.

The casing 102 is moveable in the distal direction with respect to the chassis 124. However, in the initial state of the device 100, with the cap 118 in place, the chassis 124 is enclosed so that relative movement between the chassis 124 and the casing 102 cannot occur during handling of the device 100.

Operation of the device 100 will now be described with reference to FIGS. 4 to 10.

In a first operational step, the user removes the cap 118 from the casing 102, as shown in FIG. 4. Removal of the cap 118 exposes the contact face 218 of the chassis 124 at the distal end of the device 100. The contact face 218 is positioned distally beyond the open distal end 110 of the casing 102. As the cap 118 is removed, the cup part 152 of the cap 118 is withdrawn from the needle holder 140 to break the seal around the needle 144, but the needle 144 is still shrouded within the distal end of the device 100.

In a second operational step, the user grips the casing 102 and positions the contact face 218 of the device 100 against a suitable injection site. The user pushes the casing 102 towards the injection site, causing the casing 102 to move distally with respect to the chassis 124 and bringing the distal end 110 of the casing 102 into alignment with the contact face 218 as shown in FIG. 5. Distal movement of the casing 102 relative to the chassis 124 causes the trigger ramp 206 to cooperate with the latch member 204 to release the control pin 130 for movement in the distal direction under the bias of the insertion spring 202.

Referring to FIG. 6(a), which shows the proximal end of the device 100 in more detail, and to FIG. 6(b), which shows the proximal end of the chassis 124 with the casing 102 omitted, the latch member 204 comprises a plate that is received within a recessed channel 222 formed in the proximal face of the chassis cap 124a. The latch member 204 is slidable with respect to the channel 222 in a lateral direction, and is biased in the radially outward direction by a pair of flat springs 224 that project from the sides of the latch member 204 to engage with corresponding grooves 226 formed in the proximal face of the chassis cap 124a.

The latch member 204 includes a first aperture 228 that accommodates the proximal end of the shaft 198 of the control pin 130. The latch member 204 engages with the slot 208 in the control pin shaft 198 at the periphery of the first aperture 228. As shown most clearly in FIG. 6(b), the proximal end of the control pin shaft 198 is ramped so that the shaft 198 can displace the latch member 204 during assembly of the device 100, allowing the shaft 198 to pass into the first aperture 228. The latch member 204 also includes a second aperture 230, which overlies a slot 232 in the chassis cap 124a.

Upon distal movement of the casing 102 relative to the chassis 124, the trigger ramp 206 passes through the second aperture 230 of the latch member 204 and into the slot 232 in the chassis cap 124a. During this movement, an inclined surface of the trigger ramp 206 engages with the periphery of the second aperture 230, causing the latch member 204 to move radially inwards along the channel 222 in the chassis cap 124a, against the bias of the flat springs 224. This releases the control pin shaft 198 from the periphery of the first aperture 228, as shown in FIGS. 7(a) and 7(b).

Once released by the latch arrangement, the control pin 130 moves distally with respect to the chassis 124, under the influence of the insertion spring 202. Referring to FIG. 8, through engagement between the teeth 196 of the control pin 130 and the helical tracks 192 of the control sleeve 132, the control pin 130, driven by the insertion spring 202, provides an insertion means to drive distal movement of the control sleeve 132 and the carrier 126 in an insertion direction with respect to the chassis 124. The needle 144 thus advances out of the aperture 216 in the end wall of the chassis 124 and into the injection site in an insertion stroke of the device 100. Engagement of the locking strip 176 with the slots 178, 180 prevents rotation of the control sleeve 132 during the insertion stroke. Distal movement of the carrier 126 also causes compression of the retraction spring 220.

FIG. 8(a) shows the device 100 at the end of the insertion stroke, with the needle 144 projecting out of the aperture 216 at the distal end of the device 100. As a result of the distal movement of the carrier 124 and the control sleeve 132 relative to the chassis 124, the retaining pin 184 disengages from the flexible strip 176. Thus the plunger 166 is now free to move in the distal direction, under the influence of the drive spring 164, drawing the flexible strip 176 through the slots 178, 180 in the carrier 126 and the control sleeve 132.

The plunger 166 engages with the stopper 22 of the cartridge 10 to move the stopper 22 distally with respect to the carrier 126. Initially, this causes displacement of the cartridge body 12 relative to the carrier 126. As shown in FIG. 8(b), the cartridge 10 thus moves into a second position with respect to the needle assembly 128, in which the septum 18 of the cartridge 10 is pierced by the piercing member 146 to open the outlet 16 of the cartridge 10 to create a flow path for the medicament from the chamber 14 to the needle 144.

To lock the cartridge in the second position, a plurality of clip formations 234 (one of which is shown in FIGS. 8(a) and (b)) project inwardly from the distal part 126a of the carrier 126. When in the first position, before the septum 18 has been pierced, the clip formations 234 cooperate with engagement formations in the form of ridges 236a and ramps 236b formed on the coupling element 24 (see FIG. 8(a)), to guard against accidental movement between the cartridge 10 and the carrier 126. When the plunger 166 is released, the force of the drive spring 164 is sufficient to overcome the engagement between the clip formations 234 and the engagement formations 236a, 236b so that the cartridge 10 can move distally with respect to the carrier 126. The clips pass over the ramps 236b on the coupling element 24 (see FIG. 8(b)) and engage against a shoulder formed on the proximal side of the ramps 236b to lock the cartridge 10 in the second position.

Once the cartridge 10 has moved into the second position, as shown in FIG. 8(b), further distal movement of the plunger 166 causes displacement of the stopper 22 towards the needle 144 in a delivery stroke of the device 100, forcing the medicament from the chamber 14 and through the needle 144 into the injection site.

As the delivery stroke proceeds, the flexible strip 176 continues to be drawn through the slots 178, 180 in the proximal end of the control sleeve 132 and the carrier 126. Eventually, the plunger 166 reaches an activation position, as shown in FIG. 9(a). At this point, the distal displacement of the plunger 166 is sufficient to withdraw the flexible strip 176 from the slot 180 in the control sleeve 132, releasing the control sleeve 132 for rotation relative to the carrier 126.

The control sleeve 132 is biased for rotation by cooperation between the control pin 130 and the helical tracks 192. Thus, once the control sleeve 132 is free to rotate, the control pin 130 moves distally under the bias of the insertion spring 202, with the teeth 196 of the control pin 130 bearing against the inclined walls of the helical tracks 192 to drive turning movement of the control sleeve 132, as illustrated in FIG. 9(b).

The rotational damping arrangement formed by the annular recess 158 in the proximal end of the carrier 126 and the vanes 190 of the control sleeve 132 retards the turning movement of the control sleeve 132 with respect to the carrier 126. In particular, as the control sleeve 132 turns, the viscous substance in the recess 158 is displaced around the vanes 190 (not visible in FIG. 9(b)) of the control sleeve 132, dissipating energy and controlling the speed of rotation.

The activation position is reached before the end of the delivery stroke of the plunger 166. Accordingly, the plunger 166 continues to advance during the initial turning movement of the control sleeve 132, pushing the stopper 22 to the distal end of the chamber 14 of the cartridge 10 to finish the delivery stroke, as shown in FIG. 9(b). For a time after the end of the delivery stroke, the control sleeve 132 continues to rotate, as the control pin 130 remains engaged with the control sleeve 132, and the needle 144 remains in the extended position in the injection site. This allows the medicament dose to dissipate subcutaneously before the needle 144 is retracted.

Rotation of the control sleeve 132 continues until most proximal tooth 196 of the control pin 130 reaches the open distal end 192a of the respective helical track 192. At this point, which occurs when the control sleeve 132 has rotated through a predetermined angle with respect to the carrier 126, the control pin 130 disengages from the control sleeve 132 and moves into a clearance 238 at the distal end of the enlarged portion 124c of the chassis 124. Now, the insertion spring 202 is decoupled from the control sleeve 132, so that the control sleeve 132, and therefore the carrier 126, is no longer biased in the distal direction. The retraction spring 220 now acts upon the carrier 126 to move the carrier 126 proximally in a retraction direction with respect to the chassis 124, causing the needle 144 to withdraw from the injection site in a retraction stroke of the device 100. The control pin 130 impacts upon the shoulder 210 of the chassis 124 adjacent to the clearance 238 to provide an audible and tactile indication that medicament delivery is complete and that needle retraction has been triggered.

FIG. 10 shows the device 100 at the end of the retraction stroke. The needle 144 is now retracted into the chassis 124, with the tip of the needle 144 located proximally with respect to the contact face 218 to prevent further user contact with the needle 144. The device 100 can then be removed from the injection site and disposed of. The windows 114 (see FIG. 1(b), not visible in FIG. 10) in the casing 102 allow visual confirmation that medicament delivery is complete, with the stopper 22 at the distal end of the chamber 14 of the cartridge 10. At least the parts of the carrier 126 and the chassis 124 that extend between the cartridge 10 and the windows 114 may be transparent or include apertures to allow the cartridge 10 to be seen.

Various alternative mechanisms for controlling the operations of the device may be used. For example, FIGS. 11 to 13 show a device 300 according to a second embodiment of the invention, in which an alternative mechanism for triggering the insertion stroke is provided. The device 300 of FIGS. 11 to 13 is otherwise similar to the device 100 of FIGS. 1 to 10, and like reference numerals are used for like parts.

FIG. 11 shows a proximal end part of the device 300. In this case, a latch arrangement for the control pin 130 is not provided, and the shaft 398 of the control pin 130 does not require a slot. Instead, the control sleeve 132 is latched to the end cap 324a of the chassis 124. Referring additionally to FIGS. 12 and 13(a), a pair of latch arms 404 project proximally from the cap part 332b of the control sleeve 132 and pass through corresponding apertures 408 in the chassis end cap 324a. Each latch arm 404 has a clip formation 405 at its proximal end that engages with the periphery of the corresponding aperture 408 in the chassis end cap 324a to latch the control sleeve 132 to the chassis 124. Each clip formation 405 has a ramped proximal face for deflecting the latch arm 404 during assembly of the device 300.

Figure 13B:
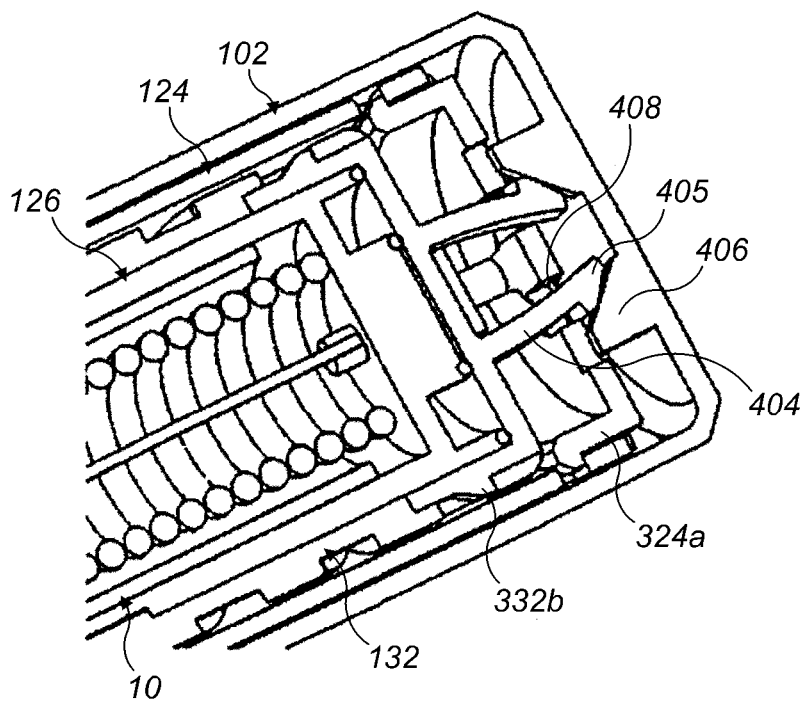
Figure 13C:
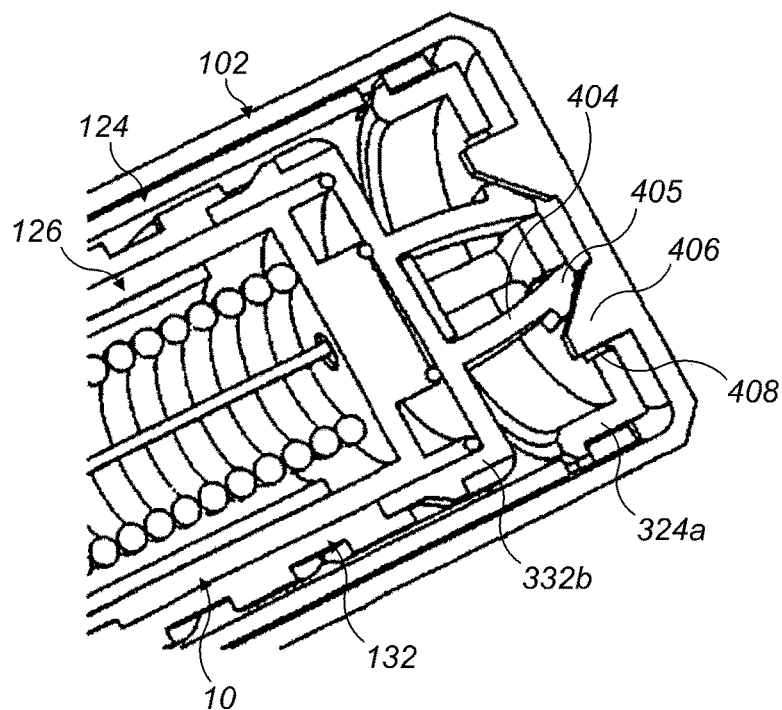

As can be seen most clearly in FIG. 13(a), a pair of trigger ramps 406 extend distally from the proximal end of the casing 102. When the casing 102 is moved distally with respect to the chassis 124 to start the operating sequence of the device 300, the trigger ramps 406 engage with the latch arms 404 to deflect the latch arms 404 inwardly, as shown in FIG. 13(b). The apertures 408 in the chassis end cap 324a are extended to accommodate the distal movement of the trigger ramps 406. As distal movement of the casing 102 continues, the clip formations 405 disengage from the chassis end cap 324a, as shown in FIG. 13(c). This releases the control sleeve 132, and therefore the carrier 126 and the cartridge 10, for distal movement with respect to the chassis 124.

As in the first embodiment of the invention, in this second embodiment distal movement of the control sleeve 132 is driven by the insertion spring 202 (see FIG. 11), the force of which is transmitted to the control sleeve 132 by way of the control pin 130.

Figure 13D:
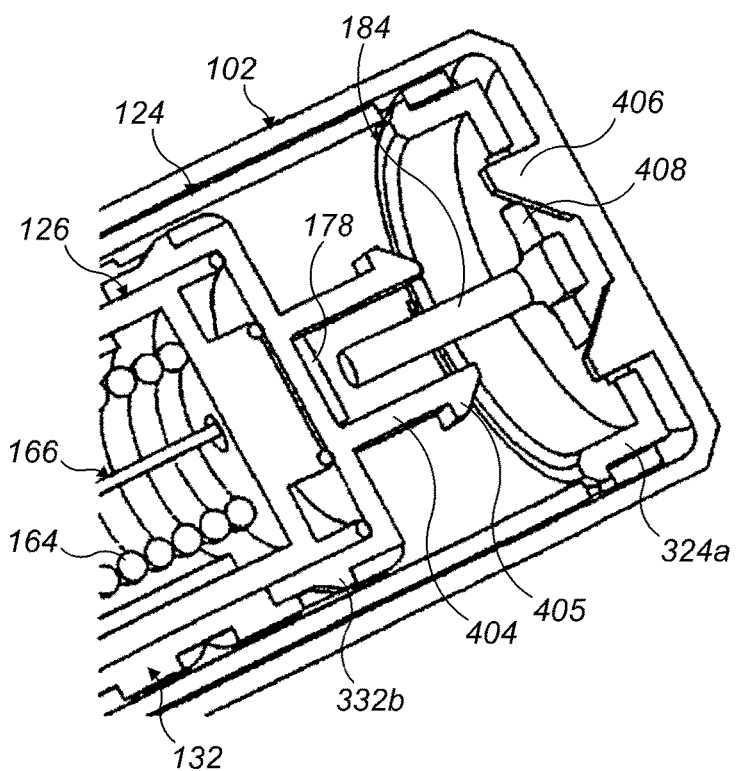

After the control sleeve 132 disengages from the chassis 124, operation of the device 300 proceeds in the same way as in the first embodiment. Thus, release of the plunger 166 occurs when the retaining pin 184 withdraws from the flexible strip 176, as shown in FIG. 13(d). Further operational steps are as described above with reference to FIGS. 1 to 10.

FIGS. 14 to 23 show a device 400 according to a third embodiment of the invention. The device 400 of FIGS. 14 to 23 is similar to the device 100 of FIGS. 1 to 10, and like reference numerals are used for like or corresponding parts. That said, in this embodiment, some alternative mechanism arrangements are used. In particular, an alternative locking element 176, coupling member 130, and insertion spring latch 204 is described.

In this third embodiment, the drive element plunger 166, shown in FIGS. 23(a), (b) and (c), is provided as a telescopic assembly with locking element 176. The drive element plunger 166 comprises a shaft part 168, which is slidably received within a channel 165 formed in locking element 176. The distal end of the shaft part 168 is provided with a head part 170, and the proximal end of shaft part 168 is provided with a proximally extending latching arm 169.

FIGS. 23(a) and (b) show the shaft part 168 in its initial state, with head part 170 in its proximally retracted position relative to locking element 176. As discussed in further detail later, beneath latching arm 169, the proximal end of the channel 165 is configured to slidably receive and key into a retaining member or pin 107 that extends distally from the proximal end 106 of the device casing 102. When engaged in the initial state, the retaining member 107 prevents rotation of the locking element 176 relative to the device casing 102. At the same time, the exterior of locking element 176 defines a shape, having two outward facing lateral surfaces, for keying through slot 178 of the carrier 126 and slot 180 of the control sleeve 132 shown in FIG. 21. In the initial state, this keying therefore keeps the slots 178 and 180 in alignment for preventing relative rotation between the control sleeve 132 and the carrier 126. The distal part of the carrier 126 is splined to the casing 102 to prevent relative rotation between these parts.

Figure 23C:
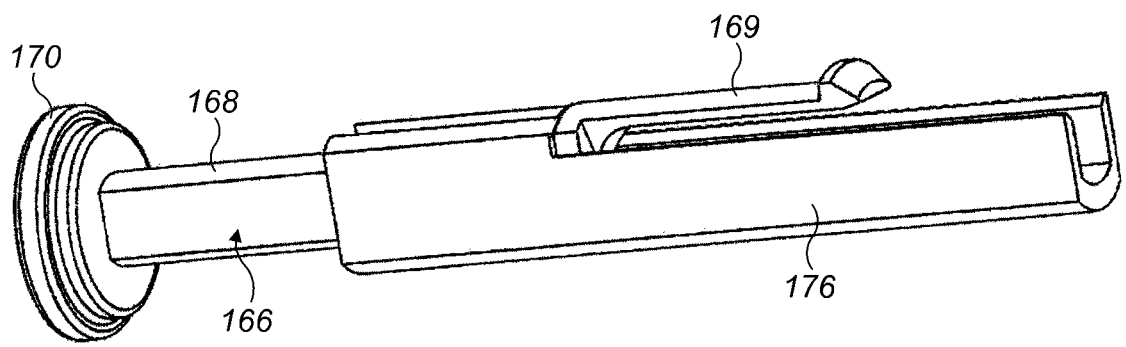

FIG. 23(c) shows the shaft part 168 in its extended state, with head part 170 slid to its distal extremity, as defined by the abutment between proximally facing shoulders 177 formed on the locking element 176 and distally facing shoulders 167 formed on the shaft part 168.

Operation of the device 400 according to the third embodiment of the invention will now be described with reference to FIGS. 14 to 23.

FIG. 14 shows the device 400 in an initial state. In a first operational step, the user removes the cap 118 from the casing 102, as shown in FIG. 15 to expose the contact face 218 of the chassis 124 at the distal end of the device 400. As shown in FIG. 15, latching arm 169 is locked behind the cap part 132b of control sleeve 132, preventing distal movement of the drive element plunger 166 relative to the control sleeve 132. At the same time, retaining member 107 extends distally from the proximal end 106 of the device casing 102 and engages into the proximal end of the channel 165 beneath latching arm 169 and thereby prevents deflection of the latching arm 169 out of its engagement with the control sleeve 132.

In a second operational step, the user grips the casing 102 and positions the contact face 218 against a suitable injection site. The user pushes the casing 102 towards the injection site, causing the casing 102 to move distally with respect to the chassis. This distal movement causes the proximal end 124a of the chassis 124 to engage with insertion spring latches 204 coupled to the coupling member 130. The coupling member 130 in this embodiment is provided in the form of a control collar. Engagement of the chassis 124 causes the insertion spring latches 204 to deflect inwardly, disengaging them from their engagement with catches 206 formed on the interior wall of the casing 102. This releases the control collar 130 for movement in the distal direction under the bias of the insertion spring 202, as shown in FIG. 15.

Once released by the insertion spring latches 204, the control collar 130 moves distally with respect to the chassis 124, under the influence of the insertion spring 202. Referring to FIG. 16, through engagement between the teeth 196 of the control collar 130 and the helical tracks 192 of the control sleeve 132, the control collar 130, driven by the insertion spring 202, provides an insertion means to drive distal movement of the control sleeve 132 and the carrier 126 in an insertion direction with respect to the chassis 124. The needle 144 thus advances out of the aperture 216 in the end wall of the chassis 124 and into the injection site in an insertion stroke of the device 400. As mentioned above, engagement of the locking element 176 with the slots 178, 180 prevents rotation of the control sleeve 132 during the insertion stroke. Distal movement of the carrier 126 also causes compression of the retraction spring 220. The distal movement of the control sleeve 132 and carrier 126 also causes the proximal end of the channel 165 to start to withdraw from its engagement with the retaining member 107. As a result, the latching arm 169 may start to deflect out of engagement with control sleeve 132 under the bias applied by drive spring 164 to the drive element plunger 166.

FIG. 17 shows the device 400 at the end of the insertion stroke, with the needle 144 projecting out of the aperture 216 at the distal end of the device 400 and the latching arm 169 having deflected out of engagement with control sleeve 132. Thus the plunger 166 is now free to move in the distal direction, under the influence of the energy released by drive spring 164. The plunger 166 engages with the stopper 22 of the cartridge 10 to move the stopper 22 distally with respect to the carrier 126. Initially, this causes displacement of the cartridge body 10 relative to the carrier 126, causing the septum 18 to be pierced by the piercing member 146 to open the outlet of the cartridge 10 to create a flow path for the medicament from the chamber 14 to the needle 144.

Once the cartridge 10 has moved into the position shown in FIG. 17, further distal movement of the plunger 166 causes displacement of the stopper 22 towards the needle 144 in a delivery stroke of the device 400, forcing the medicament from the chamber 14 and through the needle 144 into the injection site. As the delivery stroke proceeds, the shaft part 168 of the plunger 166 is moved to its extended state relative to locking element 176, as shown in FIG. 23(c), with shoulders 177 and 167 abutting. As shown in FIG. 18, this draws the locking element 176 out of the slots 178 and 180 in the proximal ends of the carrier 126 and the control sleeve 132. Eventually, the distal displacement of the plunger 166 is sufficient to withdraw the locking element 176 from the slot 180 in the control sleeve 132, releasing the control sleeve 132 for rotation relative to the carrier 126. This activation position is reached before the end of the delivery stroke of the plunger 166.

As shown in FIG. 19, the control sleeve 132 is biased for rotation by cooperation between the control collar 130 and the control sleeve's helical tracks 192. Thus, once the control sleeve 132 is free to rotate, the control collar 130 moves distally under the bias of the insertion spring 202, with the teeth 196 of the control collar 130 bearing against the inclined walls of the helical tracks 192 to drive turning movement of the control sleeve 132.

As with the first and second embodiments, the rotational damping arrangement formed by the annular recess 158 in the proximal end of the carrier 126 retards the turning movement of the control sleeve 132 with respect to the carrier 126. In this embodiment, the helical engagement of helical tracks 192 is configured to ensure that the stored position to the fully open position is less than half a revolution, thereby allowing a blind rotary damper configuration to be used. In particular, in this embodiment as shown in FIG. 21, the annular recess 158 comprises projections 190, such that the viscous substance in the recess 158 is displaced through the narrow gaps formed between the projections 190 and the recess wall as the control sleeve 132 turns. This acts to dissipate energy and control the speed of rotation, with a more effective damping constant.

As the activation position is reached before the end of the delivery stroke of the plunger 166, the plunger 166 continues to advance during the initial turning movement of the control sleeve 132, pushing the stopper 22 to the distal end of the chamber 14 to finish the delivery stroke, as shown in FIG. 22. For a time after the end of the delivery stroke, the control sleeve 132 continues to rotate, as the control collar 130 remains engaged with the control sleeve 132, and the needle 144 remains in the extended position in the injection site. This allows the medicament dose to dissipate subcutaneous before the needle 144 is retracted.

Rotation of the control sleeve 132 continues until the most proximal tooth 196 of the control collar 130 reaches the open distal end 192a of the respective helical track 192. As shown in FIG. 20, at this point, which occurs when the control sleeve 132 has rotated through a predetermined angle with respect to the carrier 126, the control collar 130 disengages from the control sleeve 132 and moves into a clearance. As the insertion spring 202 is decoupled from the control sleeve 132, the control sleeve 132, and therefore the carrier 126, is no longer biased in the distal direction. The retraction spring 220 now acts upon the carrier 126 to move the carrier 126 proximally in a retraction direction with respect to the chassis 124, causing the needle 144 to withdraw from the injection site in a retraction stroke of the device 400. The control collar 130 impacts upon the shoulder 210 of the chassis 124 to provide an audible and tactile indication that medicament delivery is complete and that needle retraction has been triggered. In an further embodiment, a further latch may be provided for latching the control collar 130 to the chassis 124 and lock the device in its retracted state.

It will be appreciated that devices according to the present invention can be readily adapted for use with different medicament viscosities and dosage volumes. For example, the strength of the drive spring can be selected to deliver the dose in a desired time, taking into account the viscosity and volume of medicament and the gauge of the needle. The length of the drive spring and the plunger can be adapted for different medicament volumes. Advantageously, the drive spring does not influence the force of needle insertion, which instead is controlled by the insertion spring.

The time delay between the end of the delivery stroke and the retraction of the needle can be controlled by various factors. In particular, the time taken for the control sleeve to rotate through the predetermined angle to decouple the insertion spring force from the carrier is determined by selectable variables, including the viscosity of the viscous substance in the damping chamber, the strength of the insertion spring, the pitch of the helical tracks, the length of the control sleeve, and so on. This allows a longer or shorter time delay to be selected, as required for a particular application. Furthermore, the activation position of the plunger, at which the control sleeve is released for rotation, can be easily adjusted by using a flexible strip of an appropriate length.

FIG. 24 shows a cross sectional view of a distal end part of a delivery device according to a fourth embodiment of the present invention. This fourth embodiment operates in substantially the same way as the third embodiment but has an alternative cap arrangement which acts to axially lock the chassis 124 relative to the casing 102, until the cap 118 has been removed. In particular, in this embodiment, the cap comprises proximally extending members 121 which are received into the distal end of the casing 102. At the same time, distal end of the casing 102 is provided with flexible fingers 123 that extend within the casing's interior in the proximal direction. The proximally extending members 121 of the cap 118 are received between the flexible fingers 123 and the main body of the casing 102, thereby bracing the flexible fingers 123 against outward deflection. Ridge formations 120 on the members 121 engage into corresponding grooves 122 on the flexible fingers 123 to provide a degree of resistance to removal of the cap 118. The flexible fingers 123 further comprise latch formations that engage into catches 125 provided on the chassis 124, thereby preventing axial movement of the chassis 124 when the device is in its initial state. As such, the device is afforded more robust drop resistance because movement of the chassis 124 is prevented by the latched engagement of the flexible fingers 123 with the chassis 124, until the cap 118 is removed. When the cap 118 is removed, the members 121 are withdrawn, thereby allowing the flexible fingers 123 to deflect outwardly as the chassis 124 is forced proximally by the user pushing the casing 102 towards the injection site.

FIGS. 25 and 26 show cross sectional views of a distal end part of a delivery device according to a fifth embodiment of the present invention. This fifth embodiment operates in substantially the same way as the third embodiment, but has a chassis locking mechanism for preventing the casing 102 from being driven proximally back once the device is activated. In particular, as discussed above in relation to the third embodiment, after triggering the device, the control sleeve 132 drives the needle forwards under the force from the insertion spring. At this stage, the force is transmitted through the control sleeve 132, the carrier 126, and the needle assembly 128 until needle assembly 128 contacts the chassis 124. At this point, the force from the insertion spring is acting between the proximal end 106 of the device casing 102 and the chassis 124 which will drive the casing 102 proximally back. However, in this embodiment, to prevent the casing 102 from being driven proximally back, a latching mechanism is provided for latching the casing 102 to the chassis 124 for preventing axial extension of these components relative to one another after the device has been activated. In this connection, FIG. 25 shows the device in an initial state, with a section of the cap 118 omitted for clarity. As shown, the chassis 124 is provided with proximally extending limbs 129 which support catches 127. At the same time, the container 102 is provided with distally projecting clips 103 corresponding to catches 127. When a user pushes the casing 102 towards an injection site, the casing 102 is moved distally with respect to the chassis 124. This movement causes the catches 127 to engage into clips 103, as shown in FIG. 26, thereby locking the casing 102 to the chassis 124. This prevents the casing 102 from being driven proximally back at the end of the injection phase. The retraction spring 220 nevertheless is able to drive the carrier 126 in a retraction direction with respect to the chassis 124, causing the needle 144 to withdraw.

Various further modifications and variations of the illustrated embodiments are possible.

For example, although not illustrated, a further spring or other biasing means may be provided to bias the casing in the proximal direction with respect to the chassis to guard against accidental operation of the device. In this case, the casing can be moved in the distal direction against the biasing force when the device is placed against the injection site. In other arrangements, a separate button or other suitable component may be provided to activate the device. For example, a trigger ramp or ramps may be provided on the distal face of a proximally-disposed button, so that displacement of the button in the distal direction with respect to the chassis releases the latch arrangement to start the insertion stroke of the device. In such cases, the chassis may also provide a casing of the device.

In the illustrated examples, the rotational damping arrangement is in a planar configuration, with the damping chamber disposed between the proximal end of the carrier and the end cap of the control sleeve. However, other arrangements are possible. For instance, a rotational damping arrangement with an annular configuration could be provided, in which the damping chamber is formed between the outer wall of the tubular body part of the carrier and the inner wall of the tubular body of the control sleeve. In this case, the damping chamber could receive inwardly-projecting vanes provided on the control sleeve.

Control of the rotational speed of the control sleeve could be achieved by providing alternative features or arrangements, instead of a rotational damping arrangement. For example, a linear damping arrangement could be provided to control the rate of distal movement of the control pin, such as by providing a piston and cylinder arrangement disposed between the control pin and the shoulder of the chassis. It is also conceivable that the rotational speed could be controlled by friction between the control pin teeth and the tracks, and/or at the contacting parts of the control sleeve and the carrier, for example by the use of relatively high-friction coatings or materials. For some applications, the time taken for the control sleeve to rotate through the predetermined angle may provide a sufficient delay time between unlocking of the control sleeve and retraction of the needle even without a damping means or other special features for slowing the rotational speed.

In the illustrated examples, decoupling of the insertion force from the carrier is triggered by the rotation of a control part comprising a sleeve through a predetermined angle with respect to the carrier. However, the control part need not be a sleeve, and could have any suitable form, such as a ring, disc, rod, tube or other structure. The control part need not be arranged concentrically around the carrier, but could instead be accommodated in a different location.

The control pin (or other coupling member) may be coupled to the control part by any suitable arrangement. For instance, whilst a helical track in the form of groove is used in the illustrated examples, a helical rib or other coupling formation may be provided instead. In the illustrated examples, the wall of the helical track provides an inclined formation (i.e. inclined relative to the axis of rotation), so that the coupling part can be biased for rotation by the insertion spring, which acts parallel to the axis. Other inclined formations such as ribs, shoulders, grooves and so on could be used. It is also possible for the control part to be biased for rotation by alternative means, such as by an additional spring.

In the first illustrative embodiment, the locking strip is formed integrally with the plunger. To this end, the plunger shaft has a cross-shaped cross section for stiffness, and the locking strip is flat to give flexibility in one plane. However, other arrangements are possible. For example, the locking strip could be attached to the proximal end of a plunger, and the plunger shaft could have any suitable cross sectional form.

The locking strip or other locking element could be held in position with respect to the control sleeve by any suitable means. For instance, in place of the retaining pin provided in the first illustrative embodiment, the locking element may be arranged to engage with a tooth or other engagement formation provided on the outside of the control sleeve, with the locking element being held in place by an inside surface of the carrier during the insertion stroke. Movement of the control sleeve with respect to the carrier during the insertion stroke brings the tooth into register with a recess or clearance provided in the carrier, allowing release of the locking element from the tooth to allow movement of the plunger with respect to the control sleeve to start the delivery stroke. A similar arrangement can also be contemplated in which the engagement formation is provided on the inside of the carrier and the recess or clearance is disposed on the control sleeve. At the same time, alternative arrangements are also envisaged. For example, as shown in the third illustrative embodiment, the locking element may be held in position with respect to the control sleeve in its initial state by its coupling with the drive element.

Furthermore, in the third embodiment, the drive element plunger is provided as a two-part telescopic assembly. However, it will be understood that other arrangements are possible. For example, a three-part telescopic assembly may be provided to allow for a greater fill volume in the cartridge, and thereby allowing for larger medicament dosage to be delivered.

Parts that are shown and/or described as being formed as a single component could be formed from two or more components suitably connected or joined. For example, in the illustrated examples, the plunger head, shaft and flexible strip are formed as a single plunger component. However, the plunger could be formed from two or more distinct parts. Similarly, in the first embodiment, the latch member and the flat springs are integrally formed. However, the latch member could be biased by a separate spring or alternative biasing means.

Devices according to the invention may be used with cartridges that differ from the example described above, and the needle assembly may cooperate with the cartridge to open the outlet and establish fluid communication in any suitable way. For example, in place of a pierceable septum, alternative means for sealing the outlet of the chamber may be provided, such as a releasable valve. The needle assembly may therefore include a sealing element release member for cooperation with the sealing element to open the outlet.

Various alternative means may be provided for forming a seal that preserves the sterility of the proximal part of the piercing member or other sealing element release member in the initial state of the device. For example, in place of the first O-ring and the tubular throat part of the coupling element of the illustrated examples, the cartridge could be provided with a modified sealing element having a bore disposed distally with respect to the septum, with the bore being arranged to receive and form a seal around the piercing member. Further suitable arrangements are described in the Applicant's International Patent Application Publication No. WO 2017/009640, the contents of which are hereby incorporated by reference.

It is also conceivable that the device could be used with a pre-filled syringe, in which case the step of moving the medicament container distally with respect to the carrier can be omitted, and the cap can be configured to withdraw a needle shield from the pre-filled syringe upon removal of the cap from the device.

Further modifications and variations of the above-described examples are also possible without departing from the scope of the present invention as defined by the appended claims.

The invention claimed is:

1. A medicament delivery device for delivery of medicament from a container into an injection site through a cannula, the device comprising:
a chassis;
a drive element for driving a stopper of the container in a delivery stroke to expel the medicament through the cannula;
a carrier arranged for movement with respect to the chassis in an insertion direction to advance the cannula from the device and in a retraction direction to withdraw the cannula after delivery of the medicament;
insertion means coupled to the carrier for biasing the carrier in the insertion direction;
a control part biased for rotation with respect to the carrier; and
a locking element cooperable with the control part for preventing rotation of the control part with respect to the carrier in an initial state of the device,
wherein the locking element is coupled to the drive element such that the control part is released for rotation when the drive element reaches an activation position during the delivery stroke,
wherein the rotation of the control part through a predetermined angle with respect to the carrier causes decoupling of the insertion means from the carrier to allow movement of the carrier in the retraction direction after the end of the delivery stroke,
wherein the control part is coupled to the carrier for joint axial movement at least in the insertion direction,
wherein the insertion means is coupled to the carrier by way of the control part,
wherein the insertion means comprises a coupling member for engagement with the control part and an insertion spring for biasing the coupling member in the insertion direction, and
wherein the control part comprises an inclined formation for engagement with the coupling member, such that the coupling member biases the control part for the rotation with respect to the carrier.

2. The device according to claim 1, comprising retarding means for controlling speed of the rotation of the control part.

3. The device according to claim 2, wherein the retarding means comprises a rotational damper.

4. The device according to claim 3, wherein the rotational damper comprises a chamber for receiving a viscous substance and at least one vane arranged for movement through the viscous substance upon the rotation of the control part with respect to the carrier.

5. The device according to claim 4, wherein the chamber is defined at least in part by the carrier and at least in part by the control part.

6. The device according to claim 3, wherein the rotational damper comprises a chamber for receiving a viscous substance and at least one projection arranged to constrict movement of the viscous substance through the chamber upon the rotation of the control part with respect to the carrier.

7. The device according to claim 1, wherein the locking element is engageable with the control part to prevent the rotation of the control part with respect to the carrier, and wherein the locking element disengages from the control part when the drive element reaches the activation position.

8. The device according to claim 7, wherein the locking element is engageable with an opening in the control part, and wherein the locking element withdraws from the opening when the drive element reaches the activation position.

9. The device according to claim 1, wherein the locking element is flexible to adopt a non-linear storage configuration in the initial state of the device.

10. The device according to claim 1, wherein the locking element comprises an elongate extension of the drive element.

11. The device according to claim 1, wherein the locking element is an elongate member slidably coupled to the drive element.

12. The device according to claim 1, wherein the drive element reaches the activation position before the end of the delivery stroke.

13. The device according to claim 1, further comprising a retainer for holding the drive element in a starting position with respect to the carrier and for releasing the drive element to start the delivery stroke.

14. The device according to claim 13, wherein the retainer is arranged to release the drive element after movement of the carrier in the insertion direction.

15. The device according to claim 14, wherein the retainer comprises a retaining member for engagement with the locking element to hold the drive element in the starting position, and wherein the movement of the carrier in the insertion direction with respect to the chassis causes disengagement of the retaining member from the locking element.

16. The device according to claim 15, wherein the locking element comprises an aperture for receiving the retaining member.

17. The device according to claim 15, wherein the chassis comprises the retaining member.

18. The device according to claim 15, wherein the retainer further comprises a latching arm connected to the drive element and for engagement between the carrier and the retaining member in the starting position.

19. The device according to claim 1, wherein the control part is rotatable around a longitudinal axis of the carrier.

20. The device according to claim 1, wherein the coupling member disengages from the control part upon the rotation of the control part through the predetermined angle.

21. The device according to claim 1, comprising a latch for holding the carrier in an initial position with respect to the chassis, and a trigger that is operable to release the latch to allow movement of the carrier in the insertion direction.

22. The device according to claim 21, comprising a casing for receiving the chassis, wherein the casing is moveable in the insertion direction with respect to the chassis to operate the trigger to release the latch.

23. The device according to claim 22, further comprising a chassis locking mechanism between the casing and the chassis for lockably connecting the casing to the chassis once the casing has moved in the insertion direction.

24. The device according to claim 1, further comprising:
a removable cap for closing an end of a casing and for preventing movement of the casing with respect to the chassis while the cap is attached to the casing; and
a latching mechanism between the casing and the chassis for preventing the movement of the casing with respect to the chassis, wherein the removable cap prevents disengagement of the latching mechanism while the cap is attached to the casing.

25. The device according to claim 1,
wherein the carrier comprises a cannula holder for retaining the cannula;
wherein the container comprises a cartridge having a sealing element for closing an outlet of the cartridge; and
wherein the device comprises a sealing element release member that is cooperable with the sealing element to open the outlet and to establish a flow path from the cartridge to the cannula.

26. A method of treating a patient having a condition susceptible to treatment with the medicament, the method comprising:
dispensing an effective amount of the medicament to the patient utilizing the delivery device according to claim 1;
wherein the medicament is disposed in the container and is dispensed into the injection site on the patient through the cannula.

27. A medicament delivery device for delivery of medicament from a container into an injection site through a cannula, the device comprising:
a chassis;
a drive element biased for driving a stopper of the container in a delivery stroke to expel the medicament through the cannula;
a carrier arranged for movement with respect to the chassis in an insertion direction to advance the cannula from the device;
a coupling member coupled to the carrier;
an insertion spring for biasing the coupling member in the insertion direction;
a latch member operable to latch the coupling member to the chassis to hold the carrier in an initial position and to release the coupling member from the chassis upon operation of a trigger for driving the carrier in the insertion direction;
a sealing element release member engageable with the container for piercing a sealing element part of the container to establish a flow path from the container to the cannula; and
a retainer for holding the drive element in a starting position with respect to the carrier and for releasing the drive element to initiate the delivery stroke once the carrier has moved a predetermined distance with respect to the chassis under the influence of the insertion spring;
wherein, on release of the drive element, the driving of the stopper moves the container relative to the carrier to engage the sealing element release member with the container for piercing the sealing element.

* * * * *